(12) United States Patent
Kizuka et al.

(10) Patent No.: US 11,969,347 B2
(45) Date of Patent: Apr. 30, 2024

(54) METHODS, SYSTEMS, AND DEVICES FOR DEPLOYING AN IMPLANT

(71) Applicant: Evalve, Inc., Santa Clara, CA (US)

(72) Inventors: Koji J. Kizuka, Redwood City, CA (US); Scott C. Mosher, San Francisco, CA (US); Gabriel R. Gonzales, Milpitas, CA (US); Dylan Thomas Van Hoven, San Carlos, CA (US); Alexander Chu, Diamond Bar, CA (US); Erik Ross Jagger, Redwood City, CA (US)

(73) Assignee: EVALVE, INC., Santa Clara, CA (US)

( * ) Notice: Subject to any disclaimer, the term of this patent is extended or adjusted under 35 U.S.C. 154(b) by 277 days.

(21) Appl. No.: 17/317,568

(22) Filed: May 11, 2021

(65) Prior Publication Data

US 2021/0353419 A1   Nov. 18, 2021

Related U.S. Application Data

(60) Provisional application No. 63/024,367, filed on May 13, 2020.

(51) Int. Cl.
*A61F 2/24* (2006.01)
*A61F 2/95* (2013.01)

(52) U.S. Cl.
CPC .......... *A61F 2/2466* (2013.01); *A61F 2/2454* (2013.01); *A61F 2002/9505* (2013.01)

(58) Field of Classification Search
CPC .............. A61F 2/2466; A61F 2/2454; A61F 2002/9505; A61F 2/9517; A61F 2/246; A61B 17/1285
See application file for complete search history.

(56) References Cited

U.S. PATENT DOCUMENTS 5,053,043 A   10/1991  Gottesman et al.
5,078,722 A   1/1992   Stevens
(Continued)

FOREIGN PATENT DOCUMENTS

CN   1469724 A    1/2004
CN   102770080 A  11/2012
(Continued)

OTHER PUBLICATIONS

"Diving watch", Sep. 25, 2014, Retrieved from https://en.wikipedia.org/w/index.php?title=Diving_watch&oldid-627082924, Retrieved on Apr. 28, 2016, Chapter: Elapsed time controller pp. 1-13.
(Continued)

*Primary Examiner* — Katherine H Schwiker
*Assistant Examiner* — Nasheha Baset
(74) *Attorney, Agent, or Firm* — Workman Nydegger

(57) ABSTRACT

A fastening system and a deployment system for controlling translation and rotation of a deployment device are presented. A fastening system may comprise one or more components configured for arresting or restricting translation of a delivery catheter of a medical device, including a mitral valve fixation device such as the MitraClip®. A deployment system may comprise one or more components configured for locking rotation of a crimping cam to a slider to control deployment of a mitral valve fixation device.

17 Claims, 30 Drawing Sheets

(56) References Cited

U.S. PATENT DOCUMENTS

| | | | |
|---|---|---|---|
| 5,263,939 | A | 11/1993 | Wortrich |
| 5,718,714 | A | 2/1998 | Livneh |
| 5,741,286 | A | 4/1998 | Recuset |
| 5,820,631 | A | 10/1998 | Nobles |
| 5,843,103 | A | 12/1998 | Wulfman |
| 5,871,493 | A | 2/1999 | Sjostrom et al. |
| 5,873,882 | A | 2/1999 | Straub et al. |
| 5,964,717 | A | 10/1999 | Gottlieb et al. |
| 5,993,470 | A | 11/1999 | Yoon |
| 6,056,769 | A | 5/2000 | Epstein et al. |
| 6,139,214 | A | 10/2000 | Zirps et al. |
| 6,926,725 | B2 | 8/2005 | Cooke et al. |
| 7,226,467 | B2 | 6/2007 | Lucatero et al. |
| 7,563,267 | B2 | 7/2009 | Goldfarb et al. |
| 7,651,502 | B2 | 1/2010 | Jackson |
| 7,666,204 | B2 | 2/2010 | Thornton et al. |
| 8,216,256 | B2 | 7/2012 | Raschdorf et al. |
| D668,334 | S | 10/2012 | Makowski et al. |
| 8,523,881 | B2 | 9/2013 | Cabiri et al. |
| D740,414 | S | 10/2015 | Katsura |
| 9,700,445 | B2 | 7/2017 | Martin et al. |
| D809,139 | S | 1/2018 | Marsot et al. |
| 2001/0007067 | A1 | 7/2001 | Kurfess et al. |
| 2001/0022872 | A1 | 9/2001 | Marui |
| 2002/0103532 | A1 | 8/2002 | Langberg et al. |
| 2004/0044350 | A1 | 3/2004 | Martin et al. |
| 2004/0049207 | A1 | 3/2004 | Goldfarb et al. |
| 2004/0049211 | A1 | 3/2004 | Tremulis et al. |
| 2004/0087975 | A1 | 5/2004 | Lucatero et al. |
| 2004/0092962 | A1 | 5/2004 | Thornton et al. |
| 2004/0138675 | A1 | 7/2004 | Crabtree |
| 2005/0006432 | A1 | 1/2005 | Racenet et al. |
| 2005/0273160 | A1 | 12/2005 | Lashinski et al. |
| 2005/0287493 | A1 | 12/2005 | Novak et al. |
| 2006/0287643 | A1 | 12/2006 | Perlin |
| 2007/0038293 | A1 | 2/2007 | St et al. |
| 2007/0088277 | A1 | 4/2007 | McGinley et al. |
| 2007/0100356 | A1 | 5/2007 | Lucatero et al. |
| 2007/0118155 | A1 | 5/2007 | Goldfarb et al. |
| 2007/0129737 | A1 | 6/2007 | Goldfarb et al. |
| 2007/0173757 | A1 | 7/2007 | Levine et al. |
| 2008/0051703 | A1 | 2/2008 | Thornton et al. |
| 2008/0097489 | A1 | 4/2008 | Goldfarb et al. |
| 2008/0154299 | A1 | 6/2008 | Livneh |
| 2008/0167714 | A1 | 7/2008 | St et al. |
| 2009/0156995 | A1 | 6/2009 | Martin et al. |
| 2009/0281619 | A1 | 11/2009 | Le et al. |
| 2010/0044410 | A1 | 2/2010 | Argentine et al. |
| 2010/0252293 | A1 | 10/2010 | Lopano et al. |
| 2011/0208169 | A1 | 8/2011 | Nash |
| 2012/0065464 | A1* | 3/2012 | Ellis ................ A61B 17/10 600/104 |
| 2012/0089136 | A1 | 4/2012 | Levin et al. |
| 2012/0253329 | A1 | 10/2012 | Zemlok et al. |
| 2012/0330348 | A1 | 12/2012 | Strauss et al. |
| 2013/0109910 | A1 | 5/2013 | Alexander et al. |
| 2013/0304117 | A1 | 11/2013 | Sugiyama |
| 2013/0310813 | A1 | 11/2013 | Kaercher et al. |
| 2014/0012287 | A1 | 1/2014 | Oyola et al. |
| 2014/0025103 | A1 | 1/2014 | Hundertmark et al. |
| 2014/0171923 | A1 | 6/2014 | Aranyi |
| 2014/0196923 | A1 | 7/2014 | Leupert et al. |
| 2014/0276966 | A1 | 9/2014 | Ranucci et al. |
| 2015/0060516 | A1 | 3/2015 | Collings et al. |
| 2015/0272759 | A1 | 10/2015 | Argentine |
| 2016/0120672 | A1* | 5/2016 | Martin ............ A61B 17/1285 623/1.11 |
| 2016/0174979 | A1 | 6/2016 | Wei |
| 2017/0100250 | A1 | 4/2017 | Marsot et al. |

FOREIGN PATENT DOCUMENTS

| | | |
|---|---|---|
| CN | 103841899 A | 6/2014 |
| EP | 1980288 A1 | 10/2008 |
| EP | 3009103 A1 | 4/2016 |
| GB | 2222951 A | 3/1990 |
| JP | 2006-528911 A | 12/2006 |
| JP | 2013-516244 A | 5/2013 |
| JP | 2014-523274 A | 9/2014 |
| WO | 01/54618 A1 | 8/2001 |
| WO | 2003/105667 | 12/2003 |
| WO | 2006/037073 A2 | 4/2006 |
| WO | 2010/024801 A1 | 3/2010 |
| WO | 2011/082350 A1 | 7/2011 |
| WO | 2012/151543 A1 | 11/2012 |
| WO | 2014/064694 A2 | 5/2014 |
| WO | 2014/121280 A2 | 8/2014 |

OTHER PUBLICATIONS

"MitraClip Clip Delivery System IFU Instructions for Use Mitraclip System Steerable Guide Catheter Ret No. SGC01ST Clip Delivery System Ref No. CDS02ST Mitraclip System Accessories Stabilizer Ref No. SZR01ST Lift Ref No. LFT01ST Support Plate Ref No. PLT01ST", Jan. 24, 2014, Retrieved from http://web.archive.org/web/*/http://www.fda.gov/downloads/AdvisoryCommitt-ees/CommitteesMeetingMaterials/MedicalDevices/MedicalDevicesAdvisoryCommit-tee/CirculatorySystemDevicesPanel/UCM343688.pdf, Retrieved on Apr. 28, 2016, pp. 1-39.

Alfieri et al., "An Effective Technique to Correct Anterior Mitral Leaflet Prolapse," J. Card Surg., 14:468-470 (1999).

Alfieri et al., "The Edge to Edge Technique," The European Association For Cardio-Thoracic Surgery, 14th Annual Meeting, Frankfurt/ Germany, Oct. 7-11, 2000, Post Graduate Courses, Book of Proceedings.

Bhudia et al., "Edge-to-Edge (Alfieri) Mitral Repair. Results in Diverse Clinical Settings," Ann Thorac Surg, 77:1598-1606 (2004).

Bhudia, #58 Edge-to-edge mitral repair: a versatile mitral repair technique, 2003 STS Presentation, [Abstract Only], 2004.

Chinese Office Action issued in Chinese Application No. 200980158707.2 dated Sep. 9, 2013.

FDA premarket approval-MitraClip Clip delivery system, Oct. 24, 2013, Retrieved from http://www.accessdata.fda.gov/cdrh.sub.--docs/pdf10/p100009a.pdf, Retrieved on Apr. 28, 2016, pp. 1-5.

Final Office Action received for U.S. Appl. No. 14/879,726, dated Apr. 20, 2018.

Frazier et al., #62 Early Clinical Experience with an Implantable, Intracardiac Circulatory Support Device: Operative Considerations and Physiologic Implications, 2003 STS Presentation, 1 page total. [Abstract Only].

Gateliene, "Early and postoperative results results of metal and tricuspid valve insufficiency surgical treatment using edge-to-edge central coaptation procedure," (Oct. 2002) 38 (Suppl 2):172 175.

Gundry, "Facile mitral valve repair utilizing leaflet edge approximation: midterm results of the Alfieri figure of eight repair," Presented at the Meeting of the Western Thoracic Surgical Association, (1999).

Gupta et al., #61 Influence of Older Donor Grafts on Heart Transplant Survival: Lack of Recipient Effects, 2003 STS Presentation, [Abstract Only].

Leitgeb, "Safety of Electromedical Devices: Law—Risks—Opportunities," May 6, 2010, Springer Science & Business Media ISBN: 978-3-21 1-99682-9, Retrieved from https://books .google.de, Retrieved on Apr. 28, 2016, pp. 66.

Non-Final Office Action received for U.S. Appl. No. 14/879,726, dated Oct. 2, 2017.

Notice of Allowance received for U.S. Appl. No. 14/577,852, filed Apr. 25, 2018.

Notice of Allowance received for U.S. Appl. No. 14/879,726, dated Nov. 8, 2018.

Notice of Allowance received for U.S. Appl. No. 14/879,726, dated Sep. 5, 2018.

Notice of Allowance received for U.S. Appl. No. 29/505,404, dated Sep. 26, 2017.

Office Action received for U.S. Appl. No. 14/577,852, filed May 16, 2017.

(56) References Cited

OTHER PUBLICATIONS

Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 29/505,404, dated Mar. 30, 2017.
Patel et al., #57 Epicardial Atrial Defibrillation: Novel Treatment of Postoperative Atrial Fibrillation, 2003 STS Presentation, [Abstract Only].
Restriction Requirement received for U.S. Appl. No. 29/505,404, dated Jan. 3, 2017.
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tibayan et al., #59 Annular Geometric Remodeling in Chronic Ischemic Mitral Regurgitation, 2003 STS Presentation, [Abstract Only].
U.S. Appl. filed Jan. 17, 2018, Marsot et al., U.S. Appl. No. 29/633,930.
U.S. Appl. No. 14/532,494, Aug. 19, 2016, Office Action.
U.S. Appl. No. 14/532,494, dated Dec. 19, 2016, Office Action.
U.S. Appl. No. 14/532,494, dated Mar. 10, 2017, Notice of Allowance.
U.S. Appl. No. 16/263,816, filed Jan. 31, 2019, Marsot et al.

* cited by examiner

METHODS, SYSTEMS, AND DEVICES FOR DEPLOYING AN IMPLANT

CROSS-REFERENCE TO RELATED APPLICATIONS

This application claims priority to U.S. Provisional Patent Application No. 63/024,367, filed May 13, 2020, the entire contents of which are incorporated by reference herein.

BACKGROUND OF THE INVENTION

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium, a condition known as mitral valve regurgitation.

Mitral valve regurgitation has several causes. Functional mitral valve regurgitation is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bowtie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, California, USA.

The MitraClip® fixation device is typically installed using a guiding system that directs the MitraClip® to the mitral valve using a steerable delivery catheter that navigates through one or more body lumens, such as vessels of the vascular system. Often the catheter is inserted through the femoral vein, through the inferior vena cava, into the right atrium, and then through a puncture in the intra-atrial septum to the left atrium, through which the mitral valve can be accessed and treated by applying the MitraClip®.

Because of the shape of the body lumens through which the steerable delivery catheter must pass and because of the nature of treating the mitral valve, and in the interest of minimally invasive treatment, the delivery catheter should ideally be equipped with a delivery device such as a handle adapted to deliver and actuate the MitraClip® in the desired configuration and location with high reliability and precise control by a practitioner.

Because of the need for precise control over the delivery and actuation of the MitraClip®, and because of the complexity of delivery systems for guiding and applying fixation devices such as the MitraClip® in a minimally invasive manner, there is a need for improved control using a simplified operation, more reliable components, and more intuitive design of a deployment system therefor. For example, translation of the delivery catheter relative to a handle must be precisely controlled to ensure that the fixation device is properly positioned, and rotation of a slider component relative to a crimping cam must be controlled to ensure that the fixation device is deployed at the desired moment. Existing devices frequently incorporate unwieldy, easily lost, and/or difficult-to-use components to control both translation of the delivery catheter relative to the delivery catheter handle and rotation of a slider component relative to a crimping cam to control deployment of a fixation device on the distal end of the catheter.

In view of the foregoing, there is a need for an improved method, system, and device for delivering an implant that provides components for controlling both translation and rotation of a deployment system in an intuitive, easy-to-use, and reliable manner.

Accordingly, it would be desirable to provide alternative and additional methods, devices, and systems for removing or disabling fixation devices that are already installed. The methods, devices, and systems may be useful for repair of tissues in the body other than heart valves. At least some of these objectives will be met by the inventions described hereinbelow.

BRIEF SUMMARY OF THE INVENTION

Embodiments of a method, system, and device for delivering an implant according to the disclosure address the problem of delivery systems requiring simplified operation, more reliable components, and more intuitive design by providing a method, system, and device for delivering an implant that minimize a profile of the delivery device and improve the ease and effectiveness of use thereof. In embodiments, a fastening system may be provided for improving deployment of an implant, including a mitral valve fixation device such as the MitraClip®.

The problem of existing delivery devices having components that may be easily lost and being difficult to use is addressed by a fastening system according to embodiments which may comprise one or more components configured for restricting or arresting translation of a delivery catheter relative to a delivery catheter handle, thereby allowing a practitioner to accurately, easily, and intuitively control translation of the delivery catheter.

The one or more components may include, for example, a threaded ring matingly engaged with a threaded distal portion of the delivery catheter handle such that as the threaded ring is rotated in a predetermined direction, a brake component is compressed and applied between the threaded ring and an outer diameter of the delivery catheter shift, increasing friction and arresting or restricting movement of the delivery catheter shaft relative to the delivery catheter handle. Translation may be facilitated by a practitioner rotating the threaded ring in an opposed predetermined direction to reduce friction.

In other embodiments, a locking arm may rotate or pivot between locked, partially locked, and unlocked configurations to selectively permit translation of the delivery catheter shaft relative to the delivery catheter handle as a protruding portion of the locking arm is selectively arranged to compress the delivery catheter shaft, thereby increasing friction and restricting or arresting translation. In other embodiments, a screw may compress a brake component against an outer diameter of the delivery catheter shaft to selectively restrict or arrest translation.

The problem of existing delivery devices having unwieldy, easily lost, or difficult-to-use regarding rotation of a slider component relative to a crimping cam is addressed by providing a deployment system according to embodiments comprising components configured for selectively locking a slider relative to a crimping cam. In embodiments, the deployment system may comprise a cap integrally formed with the crimping cam, rotation of which relative to a slider allows a cam defined by a ring attached to the cap and crimping cam to travel within a slot defined by the slider to lock and unlock rotation between the crimping cam and the slider. In other embodiments, one or more fastening components may be releasably secured to attach a cap concentrically around a bearing surface connected to an arm positioner. The fastening components may extend through the cap and slider to lock the crimping cam relative to the slider.

In other embodiments, a cap may define pins arranged corresponding to pins defined on a slider, with inward compression of the pins decoupling the slider and crimping cam. In other embodiments, a latch may be toggled between locked and unlocked configurations to decouple the slider from the crimping cam. In embodiments, a ring transmission may define a control assembly configured to toggle between engaging a deployment gear and a slider gear, with selective engagement therewith allowing a practitioner to rotate the crimping cam to deploy the fixation device, to translate the slider similar to an arm positioner, or neither.

In embodiments, a bevel gear may be arranged orthogonal to a direction of the slider for accelerating or easing rotation of the slider relative to the crimping cam. In other embodiments, a button may be toggled between locked and unlocked configurations to couple or decouple the slider relative to the crimping cam. In other embodiments, a deployment shield may be toggled between locked and unlocked configurations in which the shield selectively prevents rotation of a cap connected to the crimping cam. In other embodiments, a wedge component may be selectively engaged to lock the slider relative to the crimping cam by a rotatable outer ring component.

In embodiments, a pull tab may be configured to pull away from the slider and thereby decouple the slider and crimping cam. In other embodiments, a handle connected to a deployment pin extending through a body of the slider and crimping cam may be configured to selectively lift away from the slider and provide leverage for removing the deployment pin.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

Figure 1:
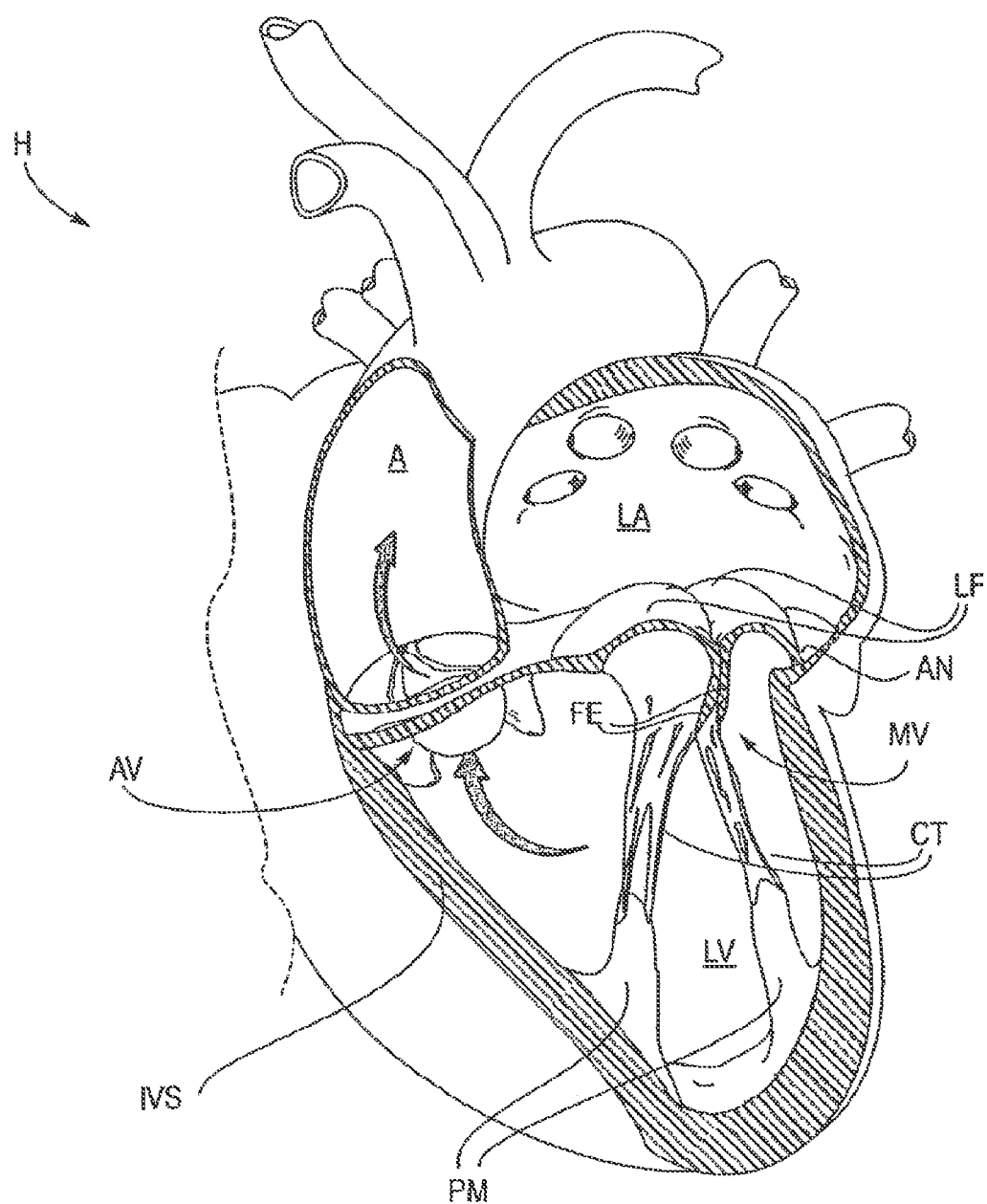
FIG. 1 illustrates the left ventricle and left atrium of the heart during systole.

The drawing figures are not necessarily drawn to scale, but instead are drawn to provide a better understanding of the components, and are not intended to be limiting in scope, but to provide exemplary illustrations. The figures illustrate exemplary embodiments of methods, systems, and devices for deploying an implant, and in no way limit the structures, configurations or functions of embodiments according to the present disclosure.

DETAILED DESCRIPTION OF THE PREFERRED EMBODIMENTS

I. Cardiac Physiology

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
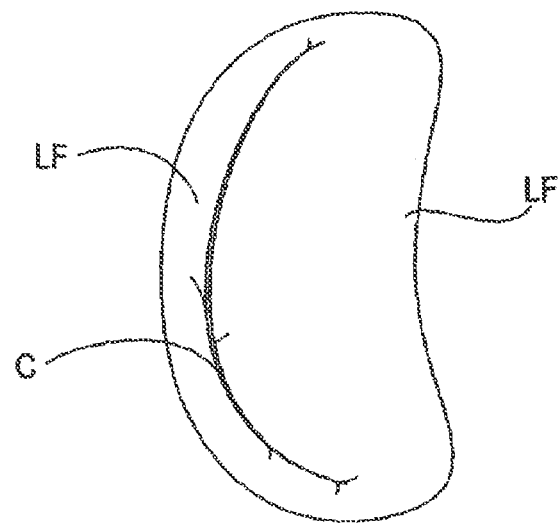
FIG. 2A illustrates free edges of leaflets in normal coaptation.
Figure 2B:
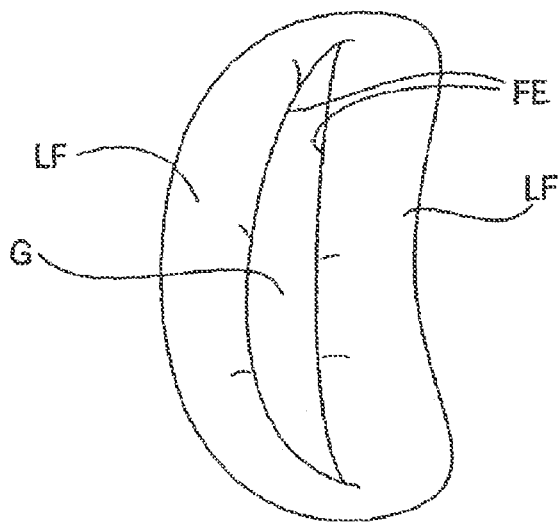
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present invention provides methods, systems, and devices for deploying an implant to treat cardiac valve regurgitation, particularly mitral valve regurgitation. The present invention also provides features that allow locking a delivery catheter relative to a delivery catheter handle and/or securing or releasing an actuator mandrel from the delivery catheter to deploy an implant device.

Figure 3A:
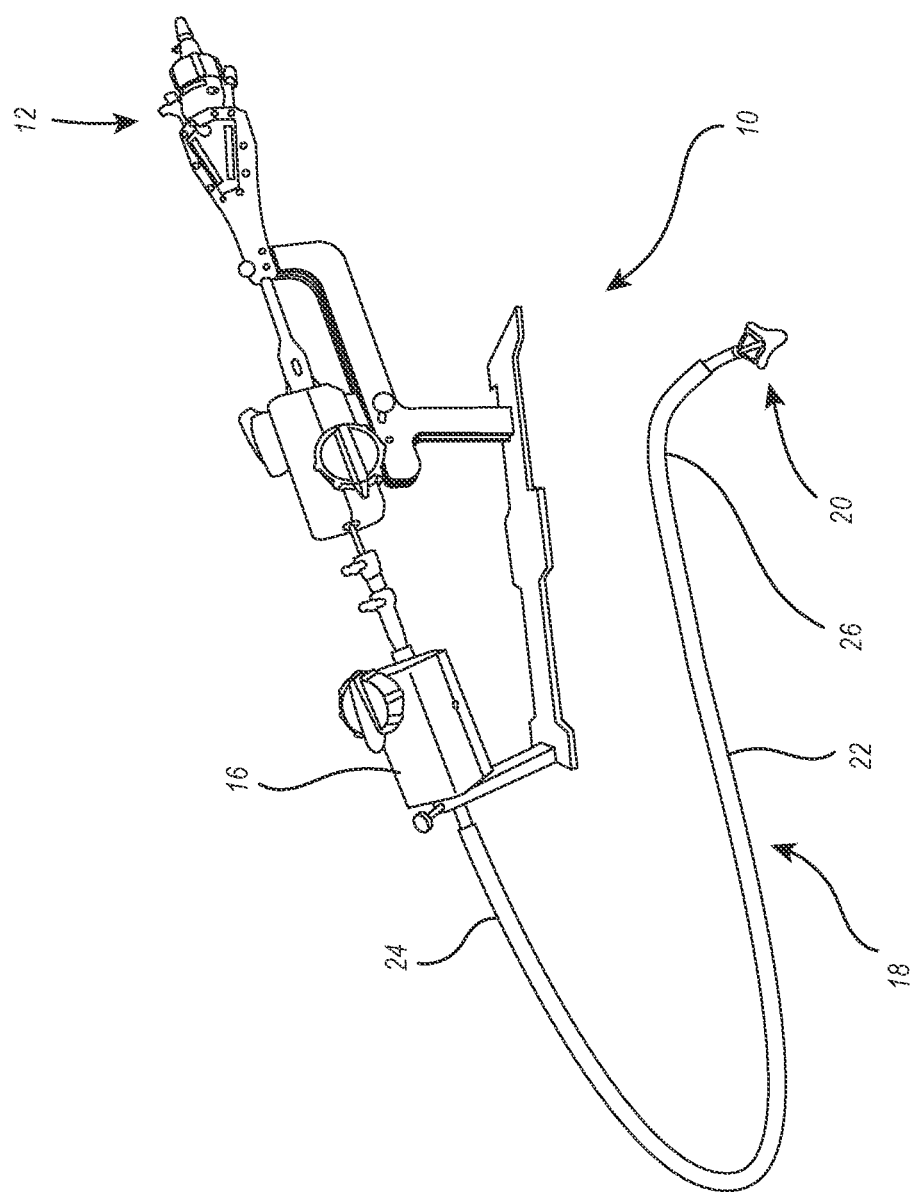
FIG. 3A illustrates in perspective view one example of a MitraClip® fixation device and delivery system.

A mitral valve fixation device 20 and delivery system 10 therefor is shown in FIG. 3A. The mitral valve fixation device 20 may be the MitraClip® or a functionally equivalent device and may be releasably supported on a distal end of a delivery catheter 18. The delivery catheter 18 attaches via one or more steerable guide handles 16 at a proximal end of the delivery catheter 18 to a delivery catheter handle 12. The mitral valve fixation device 20 may be supported on the delivery catheter 18 and the steerable guide handles 16 may operate as discussed in U.S. Pat. No. 8,945,177, granted Feb. 3, 2015, U.S. Pat. No. 7,666,204, granted Feb. 23, 2010, or U.S. Patent Application Publication No. 2017/0224319, published Aug. 10, 2017, each of which is owned by applicant and incorporated herein in its entirety by reference.

In general, the delivery catheter 18 may be manipulated by the delivery catheter handle 12 to position and orient the fixation device 20 through the body lumens and at a body location such as the mitral valve using a support base and a main body that are slidable relative to each other for providing translation of a shaft of the delivery catheter, and the main body may be rotatable about the support base to provide rotation of the shaft of the delivery catheter.

Figure 3B:
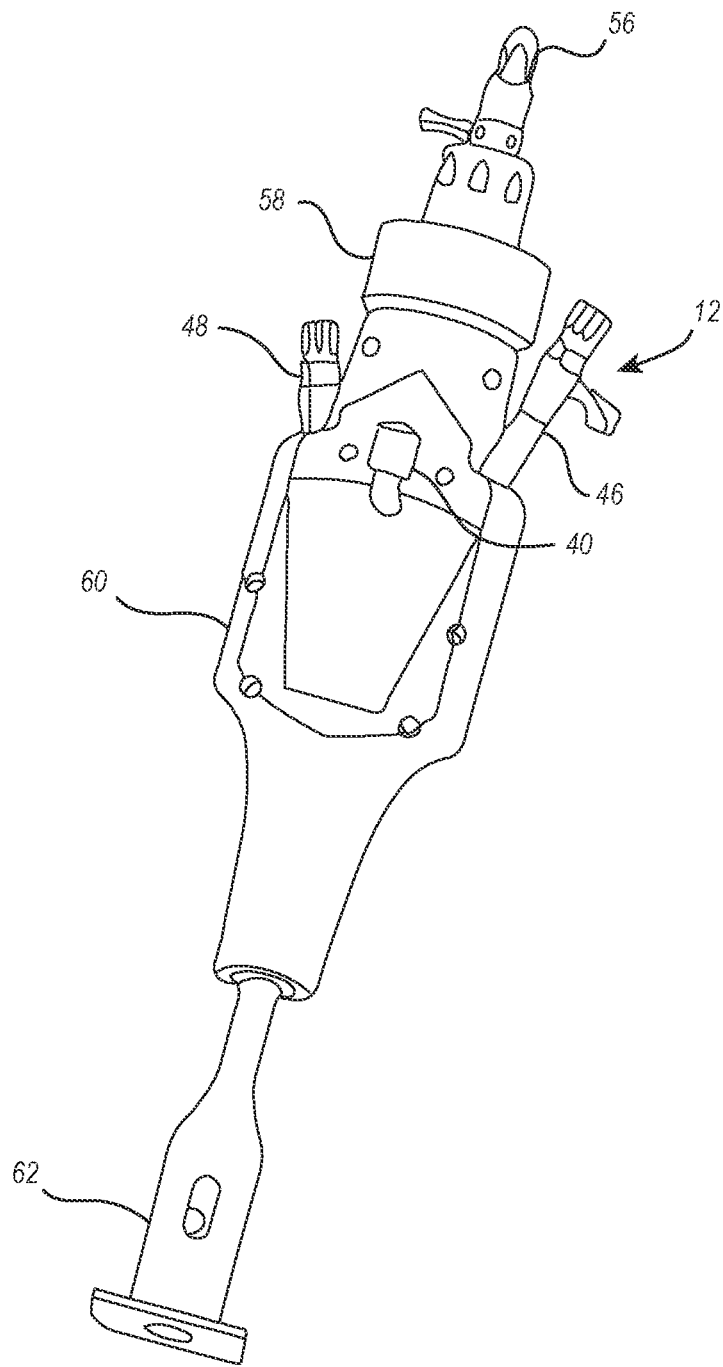
FIG. 3B illustrates in perspective view one example of a delivery catheter handle.
Figure 3C:
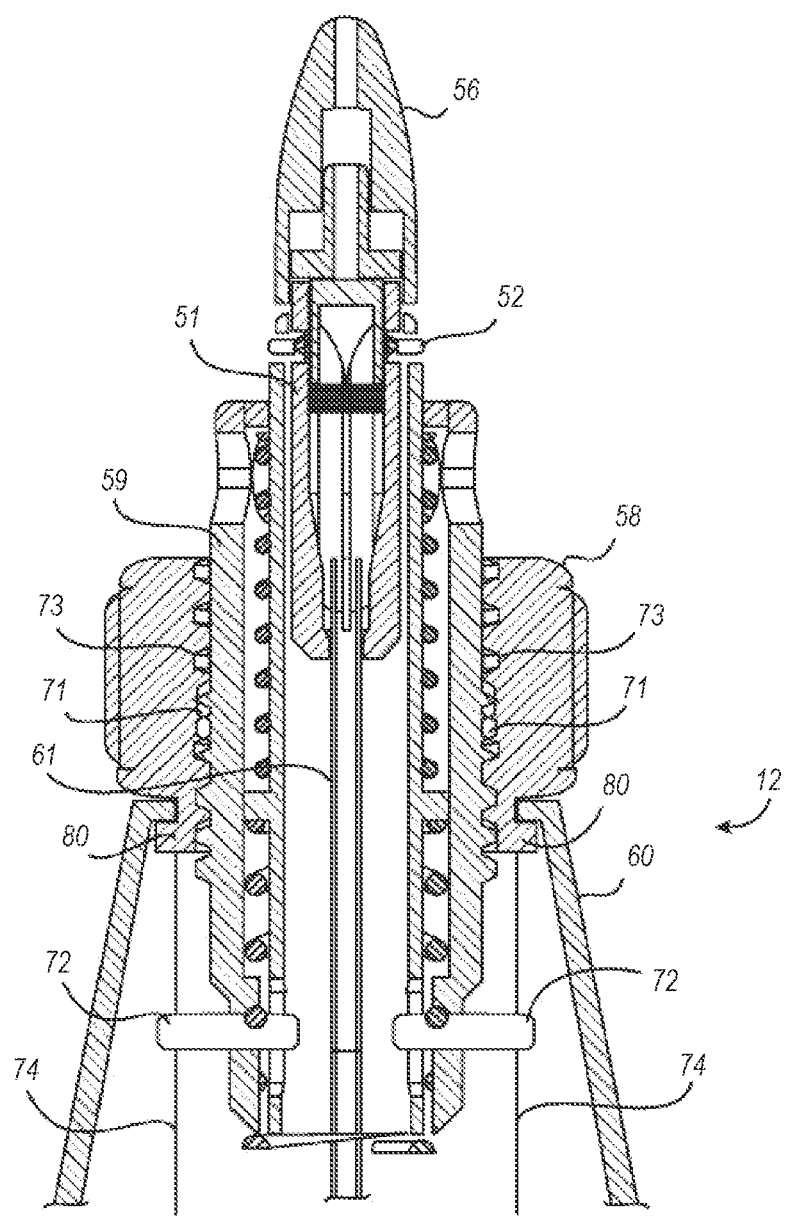
FIG. 3C illustrates in cross-sectional elevational view the delivery catheter handle of FIG. 3B.
Figure 3D:
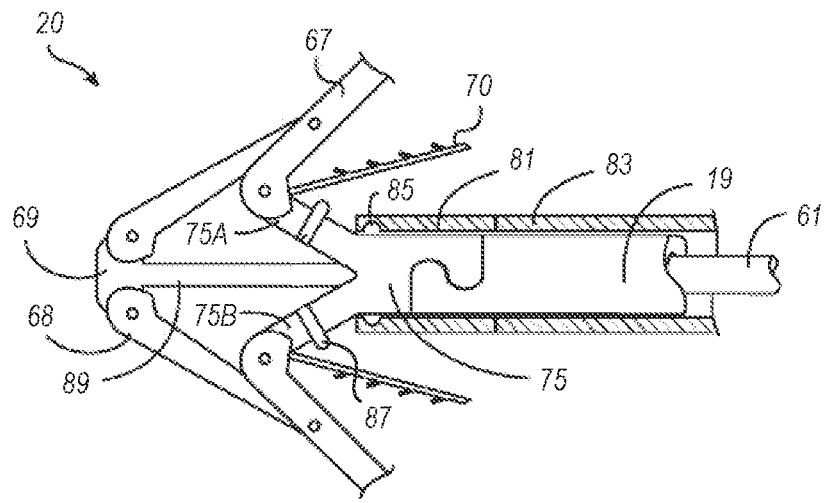
FIG. 3D illustrates in plan view a delivery catheter shaft and one example of a fixation device in an unengaged configuration.
Figure 3E:
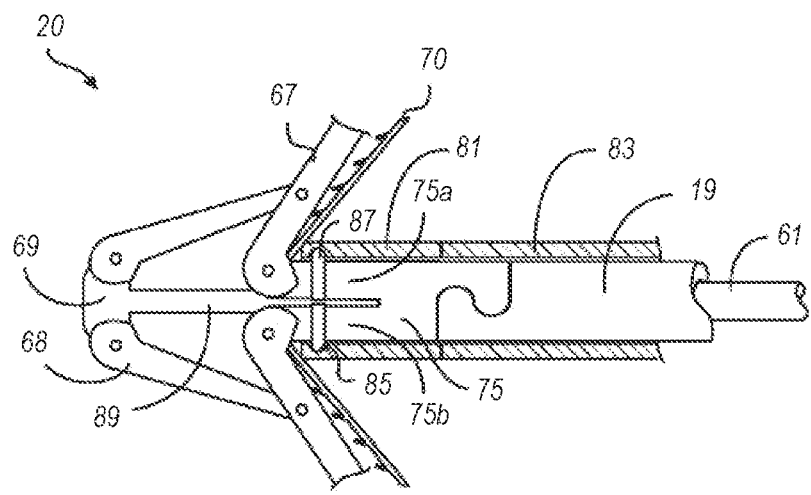
FIG. 3E illustrates in plan view a delivery catheter shaft and one example of a fixation device in an engaged configuration.

As seen in FIGS. 3D and 3E, a fixation device 20 attached distally to a delivery catheter shaft 63 and an actuator rod 61 may be deployed by manipulation of a configuration of components of the fixation device 20. In particular, the fixation device 20 may comprise proximal and distal elements 70, 67, respectively, that are coupled at one end to a respective branch 75a, 75b of a coupling member 75. Legs 68 are coupled to a base 69 and a stud 89, and at their distal ends to the distal elements 67. A collar 81 is slidably disposed over the coupling member 75 and comprises an annular groove 85 on an inner wall of the collar 81. The annular groove 85 may be arranged to slide over and engage detents 135 defined on the branches 75a, 75b. A sheath 83 is positioned coaxially over the delivery catheter shaft 19 and is slidable relative thereto to push the collar 81 over the coupling member 75.

When the delivery catheter is maneuvered into a desired position during use, the distal and proximal elements 70, 67 are in a closed configuration with the collar 81 pushed distally against but not over the detents 135 so that the branches 75a, 75b are disposed together and the fixation device 20 has a minimized profile suitable for navigating blood vessels and body lumens. When the fixation device 20 is in a position suitable for deployment, the sheath 83 is retracted so that the collar 81 slides proximally over the coupling member 75, allowing the branches 75a, 75b to separate into the position shown in FIG. 3D. The actuator rod 61 is pushed distally so as to open the distal elements 67, with the proximal elements 70 being maintained separate from the by proximal element lines (not shown).

After the proximal and distal elements 70, 67 have engaged the desired tissue, the sheath 83 may be distally advanced such that the collar 81 urges the branches 75A, 75B back together and until the groove 85 slides over the detents 87, per the position shown in FIG. 3E. The sheath 83 may then be retracted from the collar 81. Accordingly, the ability to axially translate the actuator rod 61 relative to a delivery catheter shaft 63 facilitates deployment and fixation of the fixation device 20, and control over the axial translation of the actuator rod 61 relative to the delivery catheter shaft 63 is of significant interest.

Locking of a translation of a delivery catheter relative to a delivery catheter handle advantageously provides for improved methods, systems, and devices for preventing advancement or retraction of the delivery catheter relative to the delivery catheter handle, thus enabling a practitioner to better control and navigate the placement of the fixation device supported at the distal end of the delivery catheter. Moreover, locking of translation further allows a practitioner to reliably and safely deploy the fixation device with minimized risk of unintentional translation.

According to certain of the embodiments, such selective locking or fixation of a delivery catheter relative to a delivery catheter handle is provided by way of methods, systems, and devices that may provide a variable internal diameter of a ring affixed proximate and around an outer diameter of the delivery catheter. In such embodiments, as the diameter of the ring is reduced, a compressive force is applied to the outer diameter of the delivery catheter, increasing friction and preventing unwanted movement of the delivery catheter relative to the delivery catheter handle. Although a number of embodiments are provided to achieve these results, a general overview of the basic features will be presented herein. Such features are not intended to limit the scope of the invention and are presented with the aim of providing a basis for descriptions of individual embodiments presented later in the application.

Additionally, the devices, systems, and methods of the invention provide an improved deployment system that precisely controls the release of an actuator mandrel or rod from the delivery catheter to deploy the fixation device, e.g. the MitraClip®. In embodiments, a method, system, and/or device is provided to intentionally advance or retract the delivery catheter through a variety of components, such as a crimping cam, a slider, and/or a cap. Although a number of embodiments are provided to achieve these results, a general overview of the basic features will be presented herein. Such features are not intended to limit the scope of the invention and are presented with the aim of providing a basis for descriptions of individual embodiments presented later in the application.

IV. Delivery Device

A. Overview of Delivery Device

As described above, FIG. 3 provides a perspective view of an embodiment of a delivery system 10 including a delivery catheter 18 which may be used to introduce and position a fixation device 20 as described above. The delivery catheter 18 includes a shaft 22 having a proximal end 24 and a distal end 26, and a handle 12 attached to the proximal end 24, optionally through a steerable guide handle 16. A fixation device 20 is removably securable to the distal end 26 for delivery to a site within the body, typically for endovascular delivery to the mitral valve.

The shaft 22 may define a central aperture or channel through which an actuator rod and other elements may pass from the proximal end 24 to the distal end 26. A coupling structure (not shown) may be defined or attached the distal end 26 for engaging with the fixation device 20. The shaft 22, actuator rod, and other components may be formed of any suitable material as described in at least U.S. Pat. No. 7,666,204 and/or U.S. Pat. No. 8,945,177 and/or U.S. Patent Application Publication No. 2017/0224319. In embodiments, the shaft 22 and the actuator rod may be sufficiently flexible to be navigated through the appropriate body lumens while having sufficient strength to mitigate risk of unintentional deployment.

As shown in FIGS. 3B and 3C, a handle 12 may comprise an actuator rod handle 56, an actuator rod control 58, proximal element and lock line handles 46, 48, a support base 62, a main body 60, and one or more luer connectors 40 that extend from the main body 60 into a chamber defined within the handle 12. The actuator rod handle 56 and actuator rod control 58 may actuate an actuator rod 61 extending through a central channel defined by the handle 12. Rotation of the actuator rod control 58 may cause the external threads 71 of a slider 59 to translate along corresponding internal threads 73 of the actuator rod control 58. The actuator rod control 58 is held in place by a lip 80. Pins 72 prevent rotation of the slider 59 by engaging corresponding grooves 74 which allow the slider 59 to translate.

A collet or crimping cam 51 is attached to the slider 59 and is removably attached to the actuator rod 61 at a suitable pin 52. Rotation of the actuator rod handle 56 relative to the handle body 60 facilitates the rotation of the actuator rod 61 through the corresponding rotation of the crimping cam 51. That is, the pin 52 when engaged prevents rotation of the actuator rod handle 45 and thus axial translation of the actuator rod 61, which prevents movement of the actuator rod 61 relative to the delivery catheter and subsequent deployment of the fixation device 20. Thus, the handle 12 provides for both translation and rotation of the actuator rod 61 at the distal end 24 of the shaft 22 for optimal control and placement of the fixation device 20 using minimally invasive techniques.

As discussed above, while the handle 12 has been shown and described, there remains a need for improved methods, systems, and devices for deployment of a fixation device, such that the rotation and actuation of the actuator rod can be more robustly, reliably, and intuitively controlled while maintaining a minimized profile of the deployment device.

B. Translation Control

Embodiments of the disclosure provide methods, systems, and devices for deployment of a fixation device in which improved control over the advancement and retraction of the delivery catheter shaft relative to the delivery catheter handle is achieved, this preventing unintentional translation and improving the reliability, intuitiveness, and functionality of a delivery device according to embodiments, the importance of which in the context of mitral clip installations cannot be overstated.

Figure 4:
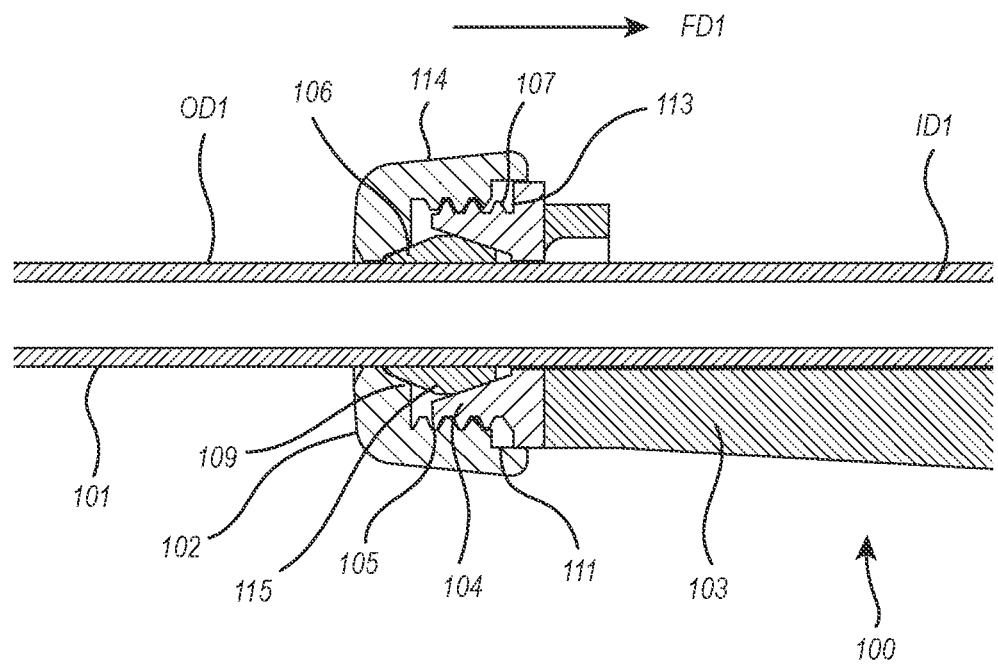
FIG. 4 illustrates in cross-sectional elevational view an embodiment of a fastening system for use with a delivery catheter handle.
Figure 5:
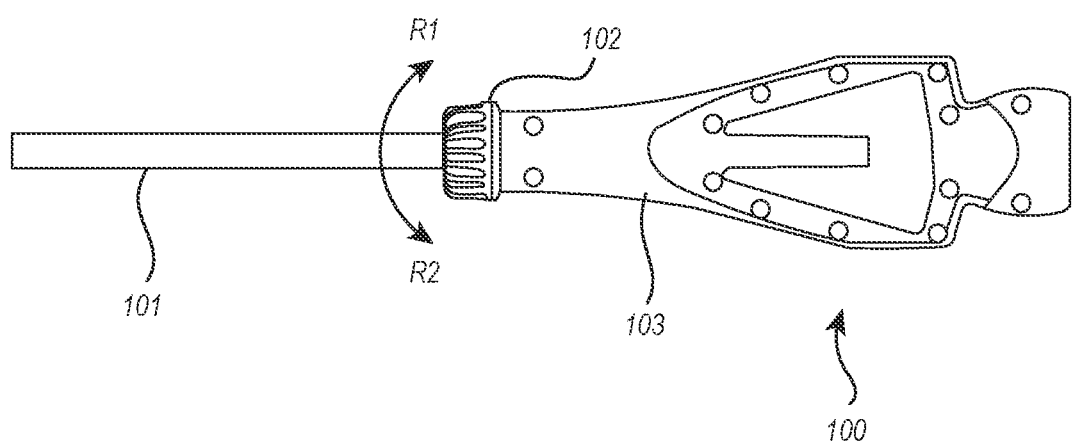
FIG. 5 illustrates in plan view the fastening system of FIG. 4.

As seen in FIGS. 4-5, a fastening system 100 may comprise a delivery catheter shaft 101 connected to a distal portion of a delivery catheter handle 103. The delivery catheter shaft 101 may comprise an outer diameter OD1 and an inner diameter ID1. Provided on the distal portion 104 of the delivery catheter handle 103 may be a threaded ring or cap 102 arranged to cooperate with the delivery catheter handle 103 to lock or fasten the delivery catheter shaft 101 relative to the delivery catheter handle 103, thereby preventing unintentional translation therebetween.

The threaded ring 102 may comprise internal threads 105 that are configured to cooperate or matingly engage with external threads 107 defined on an outer surface of the distal portion 104 of the delivery catheter handle 103. As the threaded ring 102 is rotated about the distal portion 104 of the delivery catheter handle 103, the threaded ring 102 may translate in a longitudinal fastening direction FD1. The threaded ring 102 may comprise an engagement section 109 comprising a protruding section or stop that is configured to abut against a compression ring 106 arranged between the distal portion 104 and the threaded ring 102 and the outer diameter OD1 of the delivery catheter shaft 101. In embodiments, the engagement section 109 may define a chamfered portion of an internal surface of the threaded ring 102.

The compression ring 106 may comprise any suitable material, including but not limited to elastomeric or polymeric materials including medical-grade polymers, metal materials, ceramic materials, combinations thereof, or otherwise. The compression ring 106 may be configured to cooperate with the engagement section 109 of the threaded ring 102 to compress inwardly the delivery catheter shaft 101 and apply a compressive force thereto. The compressive force may increase friction to a predetermined level that effectively arrests or reduces translation of the delivery catheter shaft 101 relative to the delivery catheter handle 103 without damaging the delivery catheter shaft 101.

The compression ring 106 may be formed from material having increased frictional properties relative to the material defining the delivery catheter shaft 101 in predetermined proportions for arresting translation. The compression ring 106 may define an outwardly bulging profile 115 that facilitates secure engagement with the distal portion 104 and a desired predetermined level of compression by the internal surfaces of the threaded ring 102 and the distal portion 104 when the threaded ring 102 is moved in the fastening direction FD1.

The threaded ring 102 may comprise a stop-forming surface 111 that may correspond to a stop-forming surface 113 defined by the distal portion 104, which, when engaged, prevent further translation of the threaded ring 102 in the fastening direction FD1. This has the benefit of providing an indication to a practitioner that the threaded ring 102 has been adequately engaged with the distal portion 104 so as to reliably arrest translation of the delivery catheter shaft 101.

An outer surface of the threaded ring 102 may comprise textured or frictional features that enable a practitioner to more easily grip and manipulate the threaded ring 102, for example to rotate the threaded ring 102 in a first rotation or clockwise direction R1, or in a second rotation or counter-clockwise direction R2, to respectively fasten or un-fasten the threaded ring 102 relative to the distal portion 104 of the delivery catheter handle 103.

By providing an integrated fastening system 100 according to the embodiments of FIGS. 4 and 5, superfluous floating components, which in practice are easily and frequently lost, are minimized, as the threaded ring 102 in cooperation with the distal portion 104 of the delivery catheter handle 103 provide a simplified, effective, and intuitive system 100 for restricting or arresting translation of the delivery catheter shaft 101 relative to the handle 103. Additionally, the threaded ring 102 improved ergonomics and ease of repeated and precise use by the practitioner by providing a conveniently sized and located component for effectively arresting translation. To this end, the threaded ring 102 may define a sloping profile 114 with a wider base or proximal surface compared to a top or distal surface for ease of gripping and manipulating.

In an alternative embodiment of a fastening system depicted in FIGS. 6-9, a delivery catheter shaft 201 and a delivery catheter handle 203 may be arrested or restricted from translation relative to each other by a fastening system 200. The fastening system 200 may comprise a locking arm 204 that is configured to extend between locked and unlocked configurations. The locking arm 204 may comprise a proximal or head portion 206 extending from a distal or base portion 205, the distal or base portion 205 configured to rotate about a hinge 207. The hinge 207 may comprise a strut or pin extending through the distal or base portion 205 and attaching to a body of the delivery catheter handle 203. An extension portion 208 may extend between the distal or base portion 205 and the proximal or head portion 206, with both the distal and proximal portions 205, 206 having in embodiments a greater width than the extension portion 208.

As shown, the body of the delivery catheter handle 203 may define a recess 209 in which the head portion 206 may be received to minimize a profile of the handle 203, and a recess 211 in which the extension portion 208 may be received for similar purposes. The recesses 209, 211 may extend at substantially a same depth into a thickness of the body of the delivery catheter handle 203, or the recess 211 may be shallower than the recess 209 or vice versa. In embodiments, the recess 209 may extend to a depth such that a distance D4 is defined between a bottommost surface of the head portion 206 and an outermost surface of the recess 209, the distance D4 allowing for example a practitioner to insert a finger to grip and manipulate the locking arm 204 between the locking and unlocked configurations.

The head portion 206 of the locking arm 204 may define on an outer surface thereof a recess 212 generally corresponding to a shape of the head portion 206. The recess 212 may advantageously serve as a push tab for ensuring that the locking arm 204 is fully in the locked configuration when appropriate and/or desired.

The delivery catheter handle 203 may define a stop portion 213 that is configured to correspond to a detent 214 defined in an inner surface of the locking arm 204. Engagement between the stop portion 213 and the detent 214 may serve to lock the locking arm 204 in the locked configuration until a sufficient force is applied at the head portion 206 to disengage the stop portion 213 and the detent 214, and may serve as an indicator to a practitioner that the locking arm 204 is properly positioned. Proximate the detent 214 a shoulder 215 may be formed to divide generally the locking arm 204 into distinct sections; alternatively, the shoulder 215, proximal of which a thickness of the locking arm 204 is reduced relative to the locking arm 204 closer to the base portion 205, has increased flexibility.

On an opposed side of the delivery catheter shaft 201 may be a resilient element 220 which may be provided as a spring element, and an insert 222 anchoring the spring element 220. The insert 222 may be configured to be stationary relative to the body of the delivery catheter handle 203. The resilient element 220 may counteract a force applied to the delivery catheter shaft 201 by the locking arm 204, for example to apply compression on both sides of the delivery catheter shaft 201. As a protrusion 210 arranged on an inwardly facing surface of the locking arm 204 in the locked configuration presses against the outer diameter OD2 of the delivery catheter shaft 201, the resilient element 220 may resist the force applied by the protrusion 210 to apply compression on both sides of the delivery catheter shaft 201.

This may, similar to the embodiment of FIGS. 4 and 5, product a predetermined desired amount of friction sufficient and configured to arrest or restrict translation between the delivery catheter shaft 201 and the delivery catheter handle 203. This may ensure that unintentional translation does not occur during delicate operations, and further provides for the reduction of easily lost, freely floating components. That is, the locking arm 204 arrangement of the embodiment of FIGS. 6-9 is a more intuitive and easier-to-use solution for mitigating translation in an intuitive manner. Further, the simplicity of the operation of the locking arm 204 enhances the speed of transitioning between locked and unlocked configurations.

Figure 6:
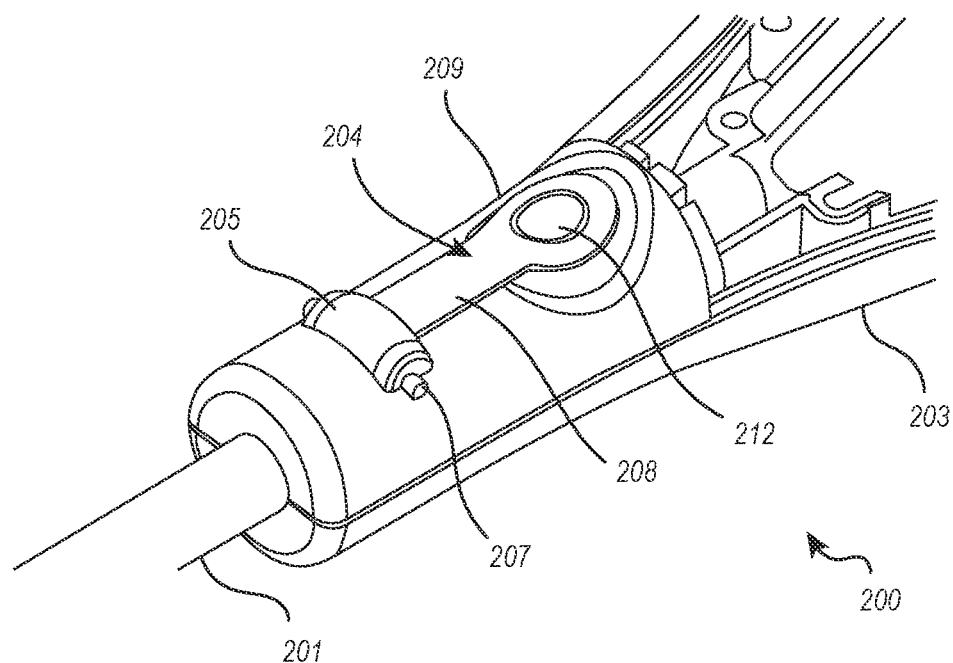
FIG. 6 illustrates in perspective view an embodiment of a fastening system for use with a delivery catheter handle, with the fastening system in a locked configuration.
Figure 7:
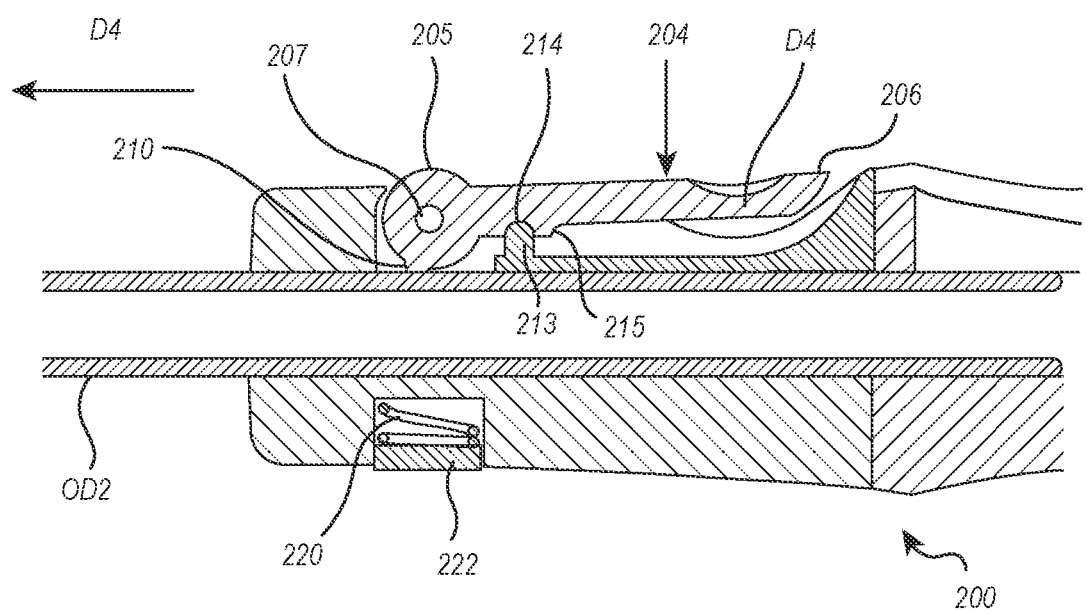
FIG. 7 illustrates in cross-sectional elevational view the fastening system of FIG. 6 in the locked configuration.
Figure 8:
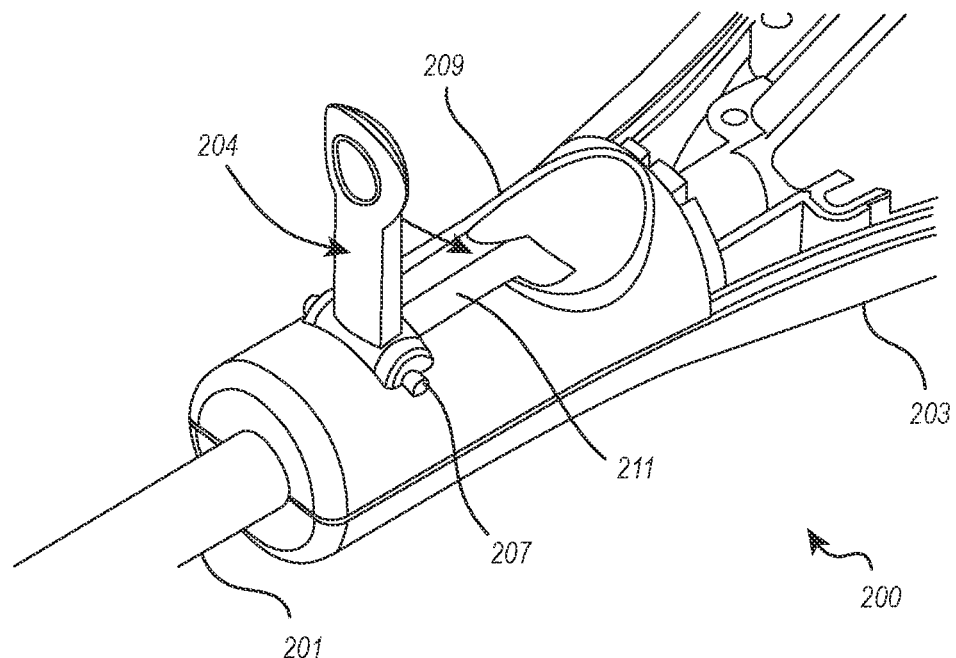
FIG. 8 illustrates in perspective view the fastening system of FIG. 6 in an unlocked configuration.
Figure 9:
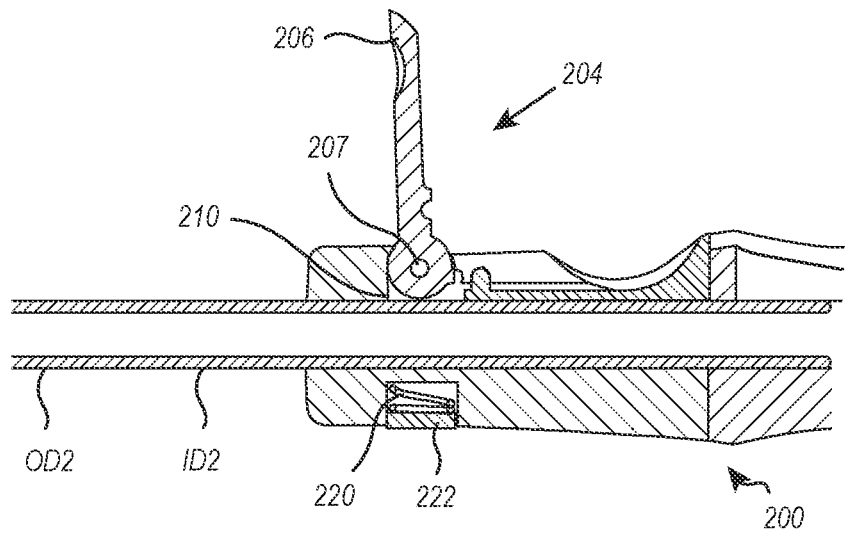
FIG. 9 illustrates in cross-sectional elevational view the fastening system of FIG. 6 in the unlocked configuration.

As seen in FIGS. 8 and 9, the locking arm 204 may pivot or rotate from the locked configuration shown in FIGS. 6 and 7 to an unlocked configuration in which compression is not applied to the outer diameter OD2 of the delivery catheter shaft 201, and free translation is permitted. As seen, the protrusion 210 is rotated away from the outer diameter OD2 such that it does not abut and apply compression thereto. The locking arm 204, by pivoting to the substantially upright position of FIGS. 8 and 9, provides a clear indicator of the status of the device to a practitioner while also providing a simple and effective manner for locking translation at the desired moment.

In addition to a locked configuration in which translation is arrested or restricted, and an unlocked configuration in which translation is freely permitted, a partially locked configuration is also contemplated. The recess 209 may be configured to provide for the partially locked configuration in which the locking arm 204 is compressed at the proximal or head portion 206 into the recess 209 and reducing the distance D4 between the head portion 206 and the recess 209. The partially locked configuration may result when a practitioner presses at the recess 212, which may through a combination of the material properties of the locking arm 204 and the force applied at the recess 212 against the stop portion 213 acting a fulcrum, temporarily move the protrusion 210 in a direction D7, disengaging the protrusion 210 from the outer diameter OD2 and permitting free translation for as long as the force is applied at the recess 212.

The embodiment of FIGS. 6-9 thus advantageously provides a simple, fast, effective, and dynamic mechanism and method for arresting or restricting translation of the delivery catheter shaft 201 relative to the handle 203, improving control of a delivery device.

Figure 10:
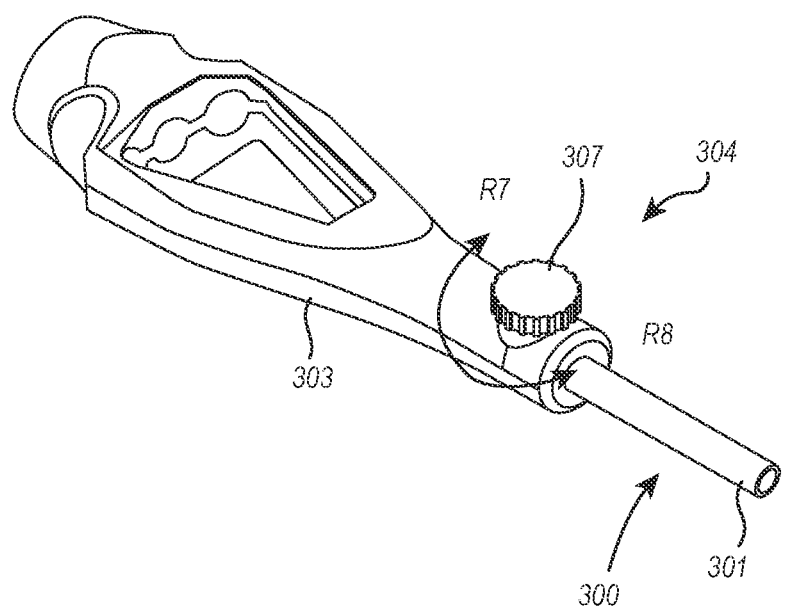
FIG. 10 illustrates in perspective view an embodiment of a fastening system for use with a delivery catheter handle.
Figure 11:
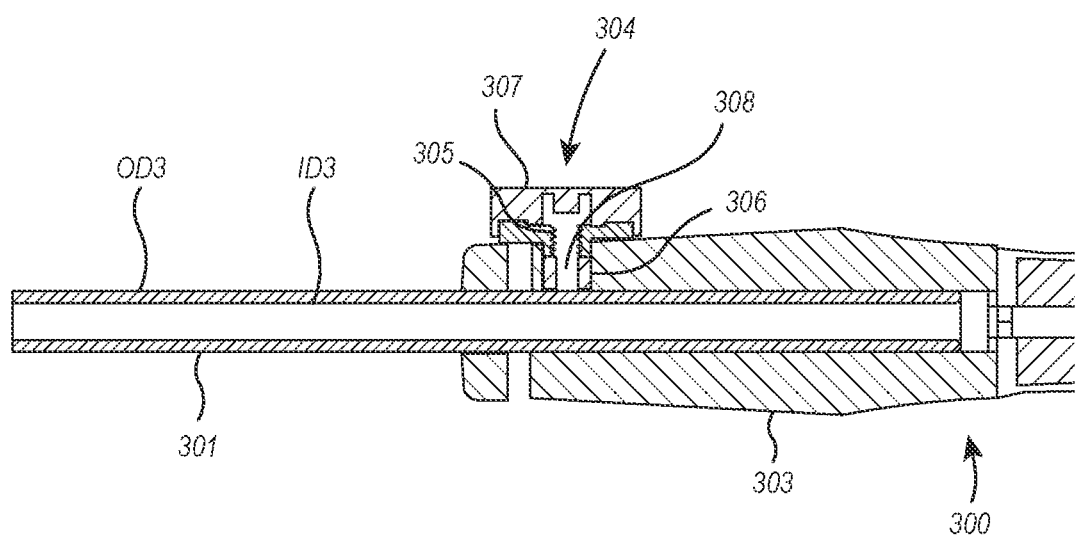
FIG. 11 illustrates in cross-sectional view the fastening system of FIG. 10.

Another embodiment is depicted in FIGS. 10-11. A fastening system 300 is depicted, the fastening system 300 comprising a delivery catheter shaft 301 that may translate relative to a delivery catheter handle 303. A fastening mechanism 304 may be formed as an integrated screw 304 provided on the handle 303 and configured to translate radially relative thereto so as to apply compression to an outer diameter OD3 of the delivery catheter shaft 301 by translating in a radial direction relative to the delivery catheter shaft 301 (in contrast to the longitudinal direction of translation of the threaded cap of the fastening system 100).

The screw 304 may comprise a cap 307 comprising a textured exterior surface configured for gripping and rotating in either a counterclockwise or rotation direction R7 or in a clockwise or rotation direction R8 to tighten or loosen the screw 304. The screw 304 may comprise a threaded element 305 connected to the cap 307 and which may cooperate with an aperture 308 defined by a body of the handle 303. An interior surface of the aperture 308 may define threadings corresponding to the threaded element 305.

Proximate the outer diameter OD3 of the delivery catheter shaft 301, a brake element 306 comprising any suitable material may be arranged and configured to apply compression to the outer diameter OD3 of the delivery catheter shaft 301 as the screw 304 is moved in an insertion direction. The compression applied by the brake element 306 under the influence of the screw 304 may provide a desired and predetermined amount of friction sufficient to arrest or restrict translation of the delivery catheter shaft 301 relative to the handle 303.

The brake element 306 may comprise, for example, a thermoplastic and/or elastomeric material having a desired coefficient of friction with the material defining the delivery catheter shaft 301, and may be formed as an annular element into which the threaded element 305 extends. It will be understood that the depicted embodiment is merely exemplary, and the brake element 306, the screw 304, and the fastening system 300 components may be formed of any suitable material in any suitable configuration.

The above described embodiments advantageously address the problem of delivery systems for fixation devices being poorly adapted to precisely, easily, effectively, and intuitively control a degree of translation between a handle and a catheter shaft of the delivery system with fewer floating components and with enhanced speed.

It will be understood that the disclosed embodiments of a fastening system are merely exemplary, and that any material, configuration, mechanism, or other feature may be used in combination with one or more features or one or more of the above embodiments according to and within the spirit and scope of the disclosure. Furthermore, the disclosed embodiments are not limited to mitral valve-related treatments or medical devices and procedures generally, but rather may extend to any suitable system, device, or method.

C. Rotation Control for Deployment of a Fixation Device

Embodiments of the disclosure provide methods, systems, and devices for deployment of a fixation device in which improved control over securing and releasing an actuator mandrel from the delivery catheter to deploy the fixation device is achieved, this preventing unintentional or improper deployment of the fixation device and thereby improving patient outcomes.

Figure 12:
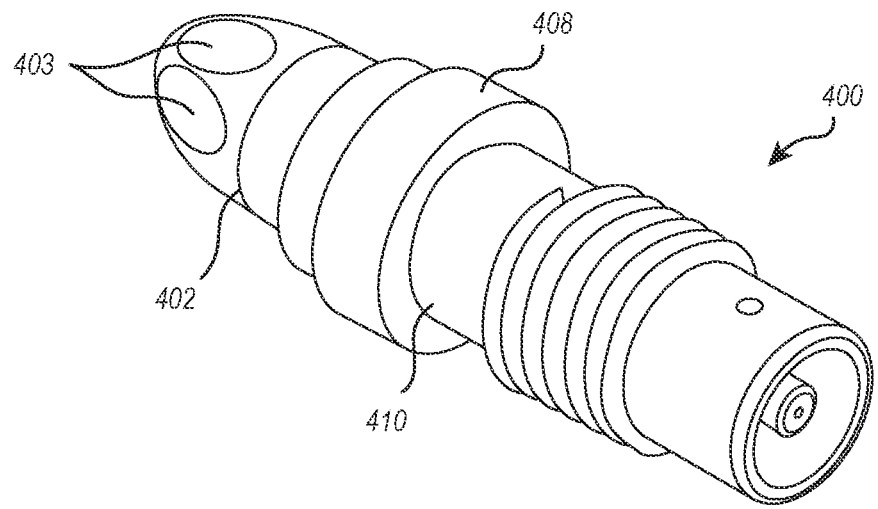
FIG. 12 illustrates in perspective view an embodiment of a deployment system for use with a delivery catheter handle.
Figure 13:
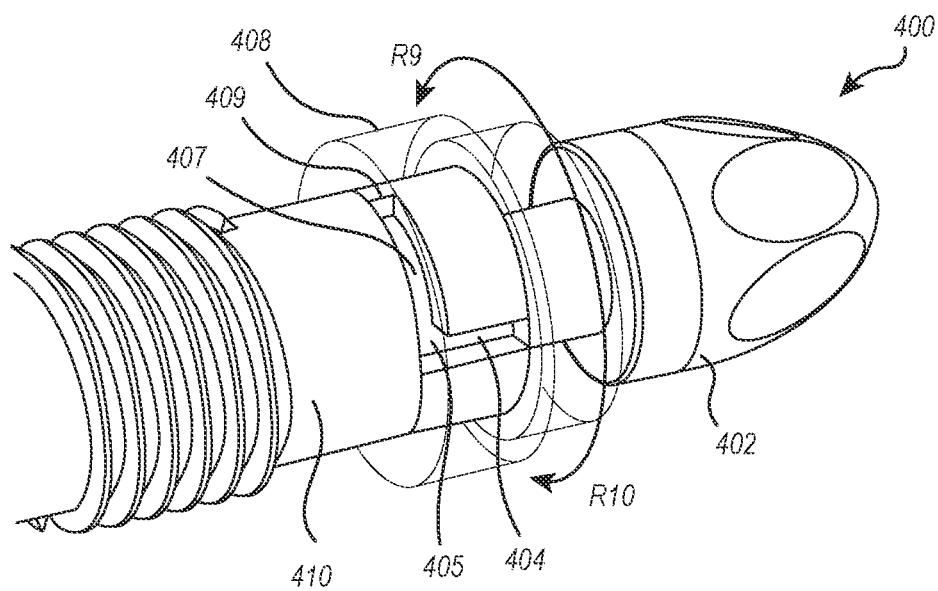
FIG. 13 illustrates in perspective view the deployment system of FIG. 12.
Figure 14:
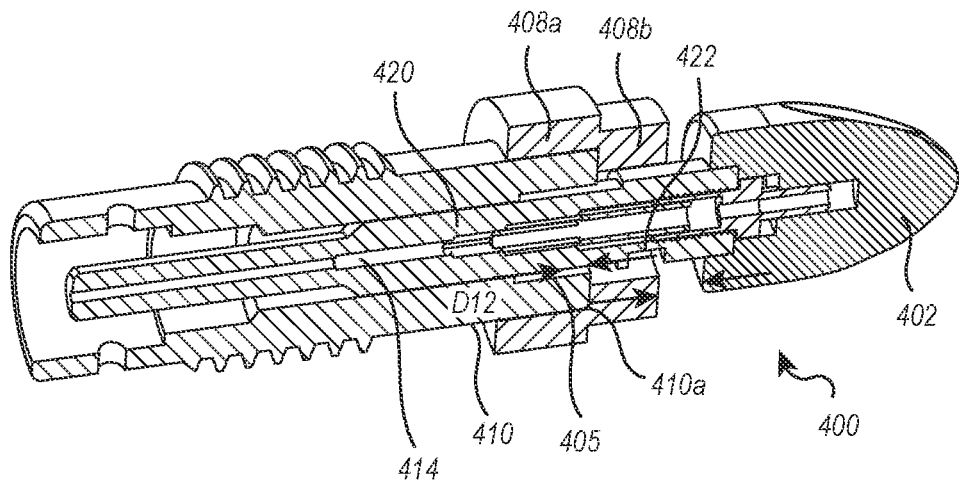
FIG. 14 illustrates in cross-sectional perspective view the deployment system of FIG. 12.

In the embodiment of FIGS. 12-14, a cap 402 is provided with a deployment system 400 comprising a slider 410 analogous to the slider described in conjunction with FIGS. 3B-3C. The cap 402 may comprise grip indentations or detents 403 enabling manipulation of the cap 402 to operate the deployment system 400. The indentations 403 may further provide indicia regarding a degree of rotation of the cap 402. The cap 402 may be attached directly to the crimping cam 420. In particular, the slider 410 may comprise a ring 408 extending generally concentrically and along an exterior surface of the slider 410. The ring 408 may be arranged and secured in any suitable manner on the slider 410.

The ring 408 comprises a cam 407 on and extending inwardly from an internal surface thereof, the cam 407 corresponding to and engaging a slot 405 defined through at least a partial thickness of a body of the slider 410. The slot 405 may define a path extending at parts longitudinally relative to the cap 402 and at times circumferentially relative to the cap 402. As with the cap 402, the ring 408 may define indicia on an outer surface to indicate a position of the cam 407 to a practitioner. The ring 408 may further comprise distinct ring portions which may have different diameters.

For example, a first ring component 408a may have a larger diameter relative to the outer surface of the slider 410 than a second ring component 408b, and may extend distally of the second ring component 408b. The ring components 408a, 408b may be integrally formed or may be distinct components secured to each other in any suitable manner. In embodiments, the second ring component 408b may extend inwardly a greater distance than the first ring component 408a, abutting a shoulder 410a of the slider 410.

The configuration of the slot 405 allows a practitioner to rotate the ring 408 in either clockwise or counterclockwise rotation directions R9, R10 as appropriate to create interference with and lock a crimping cam 420 disposed internally to and cooperating with the slider 410. In an embodiment, the slot 405 is configured such that a stop-forming terminal 409 is defined in a clockwise direction R9 relative to a longitudinally extending portion 404 of the slot 405, such that as the ring 408 is rotated in the clockwise direction R9, the cam 407 eventually engages the stop-forming terminal 409.

Conversely, as the ring 408 is rotated in an opposed counterclockwise direction R10, the cam 407 eventually may engage the longitudinally extending portion 404 of the track 405, this preventing further circumferential rotation of the ring 408. A distance D14 defined between a proximal surface of the ring 408 and a distal surface of the cap 402 facilitates a proximal translation of the ring 408 to allow the cam 407 to travel a corresponding distance D12 through the longitudinally extending portion 404. After traveling longitudinally through the longitudinally extending portion 404, the cam may engage a stop-forming detent 422 defined by at least part of a thickness of the crimping cam 420.

The cam 407 may have any suitable configuration, size, and placement on the ring 408. In FIG. 13 the cam 407 is shown extending near a distal portion of the ring 408, but is not limited thereto. When the cam 407 interferes with the rotation of the crimping cam 420, rotation of the actuator rod 414 is arrested for deployment of the fixation device. This arrangement advantageously obviates the need for a pin component cooperating with an integrated locking mechanism between the crimping cam 420 and the slider 410, reducing the number of floating and potentially broken or misplaced components, and generally simplifying the operation of the deployment system 400 without compromising on the effectiveness of the deployment system 400.

Figure 15:
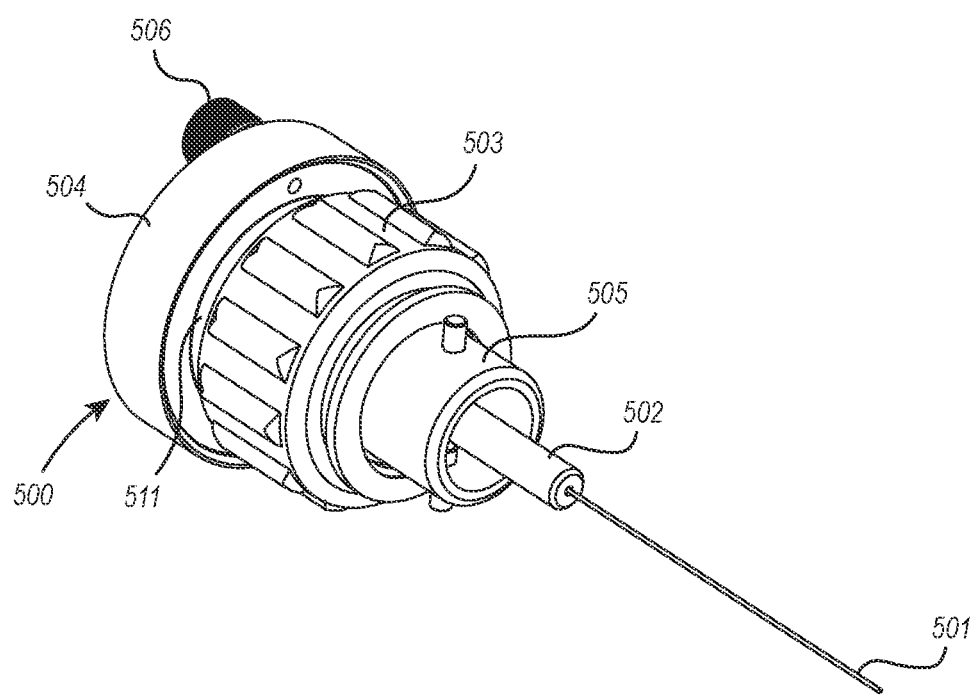
FIG. 15 illustrates in perspective view an embodiment of a deployment system for use with a delivery catheter handle.
Figure 16:
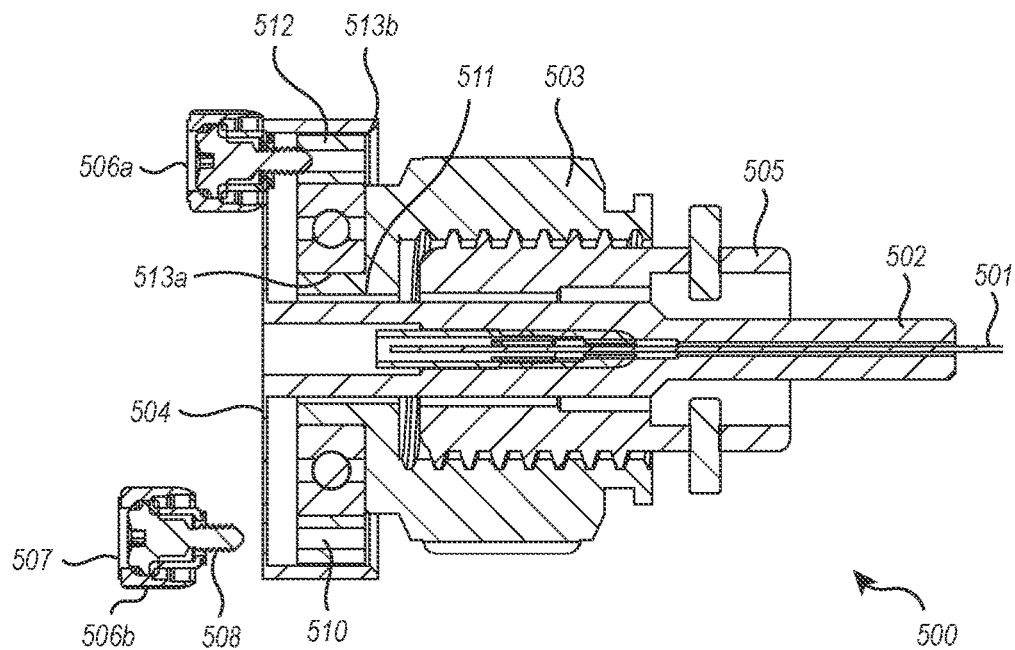
FIG. 16 illustrates in cross-sectional plan view the deployment system of FIG. 15.
Figure 17:
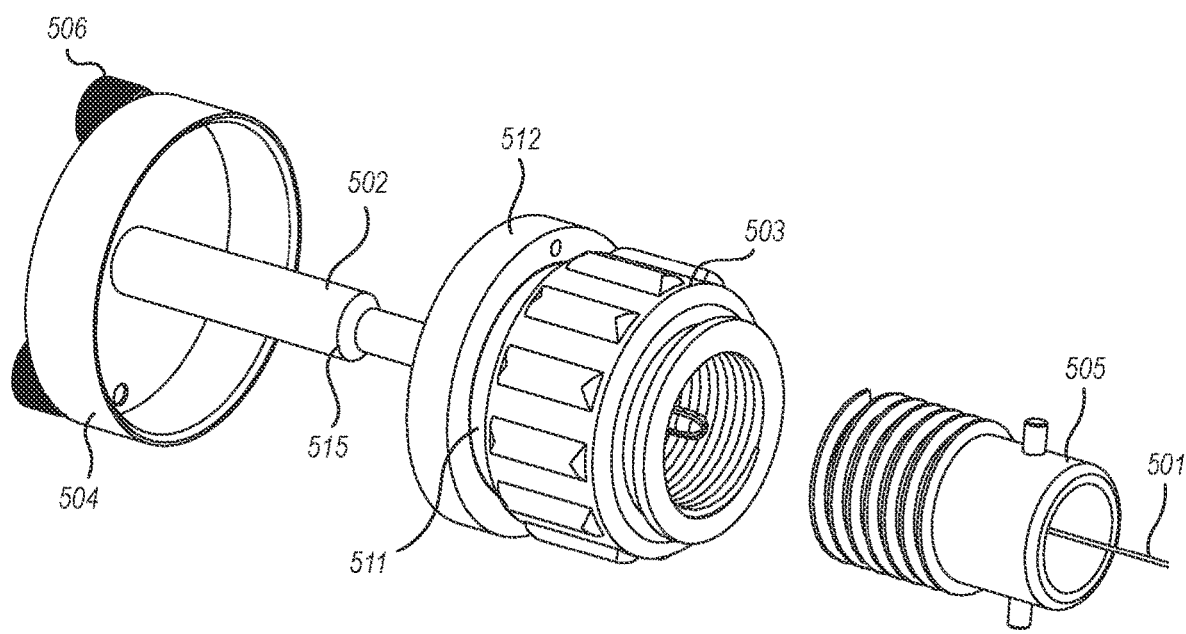
FIG. 17 illustrates in exploded view the deployment system if FIG. 15.

In an alternative embodiment depicted in FIGS. 15-17, a deployment system 500 may comprise a cap 504 having one or more fastening components 506 that releasably connect the cap 504 to a bearing surface 512 at one or more junctions 511 and which, in turn, is connected to an arm positioner 503 configured for translation of the rod 501 within a crimping cam or collet 502 comprising at least one shoulder 515. The crimping cam 502 may be directly connected to or integrally formed with the cap 504.

A slider 505 may likewise be configured to cooperate with the arm positioner 503 to effect translation of the actuator rod 501. The cap 504 may attach over and/or around the bearing surface 512 in a substantially concentric manner, with the inner diameter of the cap 504 and the outer diameter of the bearing surface 512 correspondingly configured. The cap 504, when attached, may abut the bearing surface 512 at one or more junctions 513a, 513b.

The fastening components 506 may be screws comprising a handle 507 connected to a threaded element 508. A corresponding threaded aperture 510 may be defined through at least part of a thickness of the cap 504 and the bearing surface 512. In a locked configuration shown in FIG. 15 and regarding the fastener 506a, the threaded element 508 extends through the cap 504 and into the bearing surface 512 to lock rotation of the crimping cam 502 relative to the slider 505. By contrast, in the unlocked configuration shown in FIG. 16 regarding the fastener 506b, the cap 504 does not prevent rotation of the crimping cam 502 relative to the slider 505, facilitating deployment of the fixation device at a distal end of the actuation rod 501.

This arrangement advantageously facilitates deployment of the fixation device in an intuitive and controlled manner and further results in deployment of the fixation device similar to opening and closing the clip of the fixation device.

Figure 18:
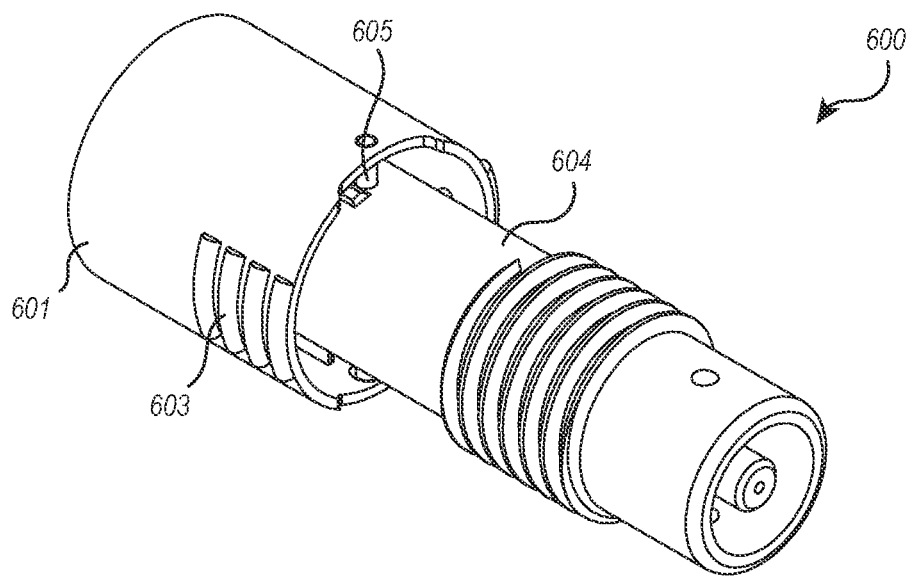
FIG. 18 illustrates in perspective view an embodiment of a deployment system for use with a delivery catheter handle.
Figure 19:
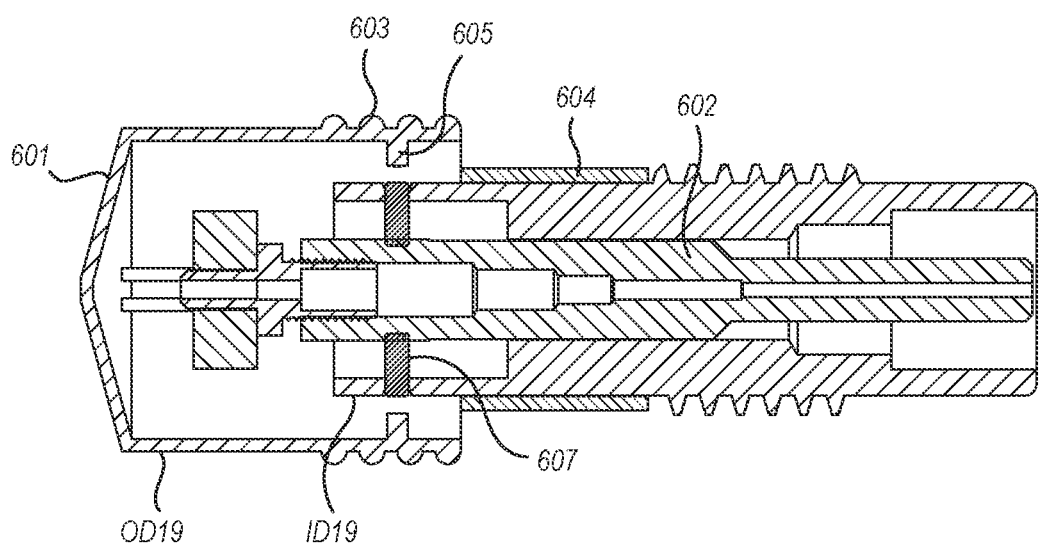
FIG. 19 illustrates in cross-sectional plan view the deployment system of FIG. 18.
Figure 20:
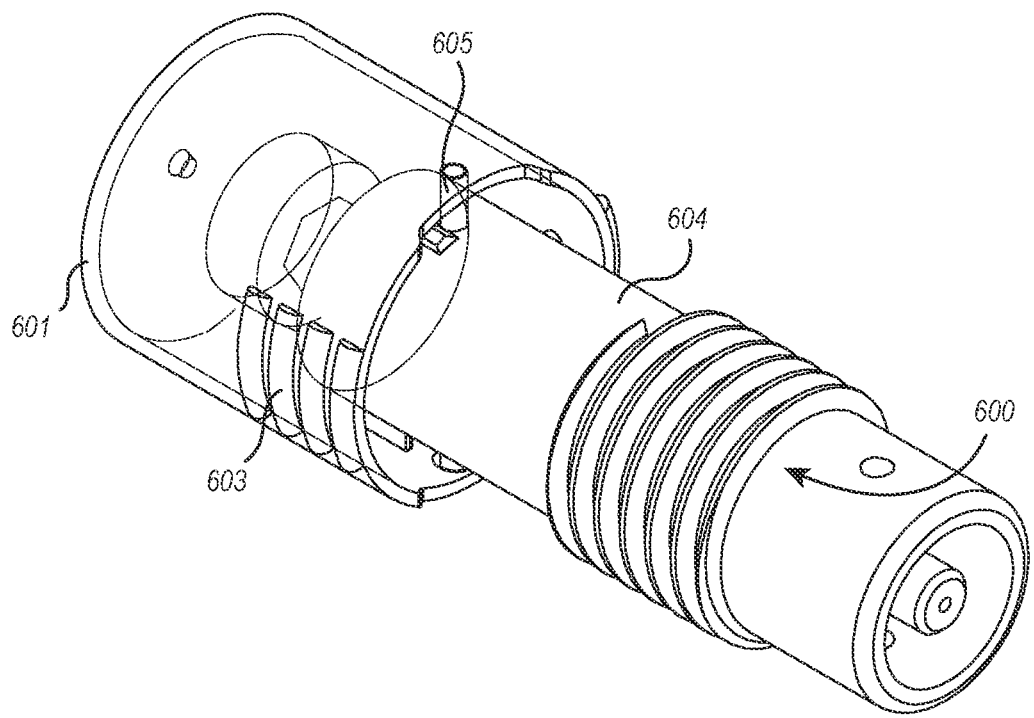
FIG. 20 illustrates in perspective view the deployment system of FIG. 18.

An alternative embodiment of a deployment system is shown in the embodiment of FIGS. 18-20. A deployment system 600 may comprise a crimping cam 602 held stationary by a set of pins 605 which interface between a slider 604 and the crimping cam 602. The pins 605 may be provided on an interior surface of a cap 601 configured to extend over and/or around a surface of the slider 604 in a substantially concentric manner.

The pins 605 of the cap 601 may be aligned with pins 607 of the slider 604 such that by compression an exterior surface OD19 of the cap 601, for example at compression or textured portions 603, the pins 605 of the cap 601 push the pins 607 of the slider 604 inwardly within channels 609 defined by the crimping cam 602. This may, at a predetermined amount of inward movement of the pins 607, result in decoupling of the slider 604 and the crimping cam 602.

Likewise, when the cap 601 is not compressed against the pins 607 of the slider 604, tension in the system returns the pins 607 to an original position, retaining engagement between the slider 604 and the crimping cam 602. For example, resilient elements such as springs may be provided in the channels 609 to bias the pins 607 outwardly to engage the slider 604 and the crimping cam 602. Textured features such as ribs and corresponding rivulets defined by the outer surface of the cap 601 at the compression portions 603 may both serve as indicators of where to apply compression but may also provide increased friction to better facilitate grip and manipulation of the cap 601.

In embodiments, the deployment system 600 may be configured such that a practitioner may pinch or compress the cap 601 at the compression portions 603 and then turn the cap 601 relative to the slider 604 to deploy the fixation device. The material defining the cap 601 may be any suitable material, and in embodiments may have greater flexibility proximate the compression portions 603 allowing the cap 601 to bend inwardly under compression or forces applied by the practitioner's fingers.

The arrangement of the deployment system 600 may advantageously reduce the number of steps required to deploy a fixation device relative to existing devices as well as the number of components required to effect deployment. For instance, a pin preventing rotation of the crimping cam relative to the slider is no longer needed but rather the modality for effecting rotation is integrated with the cap.

Figure 21:
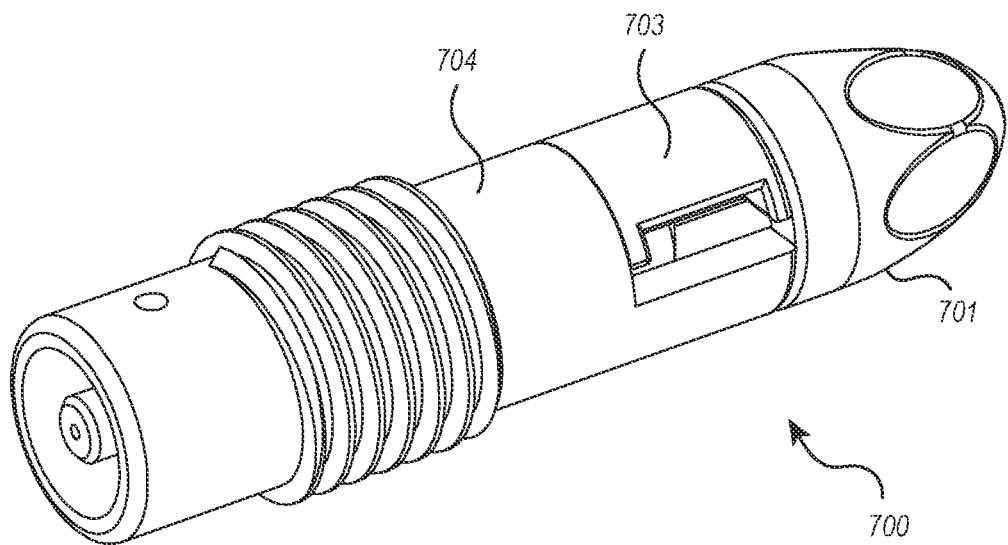
FIG. 21 illustrates in perspective view an embodiment of a deployment system for use with a delivery catheter handle in a locked configuration.
Figure 22:
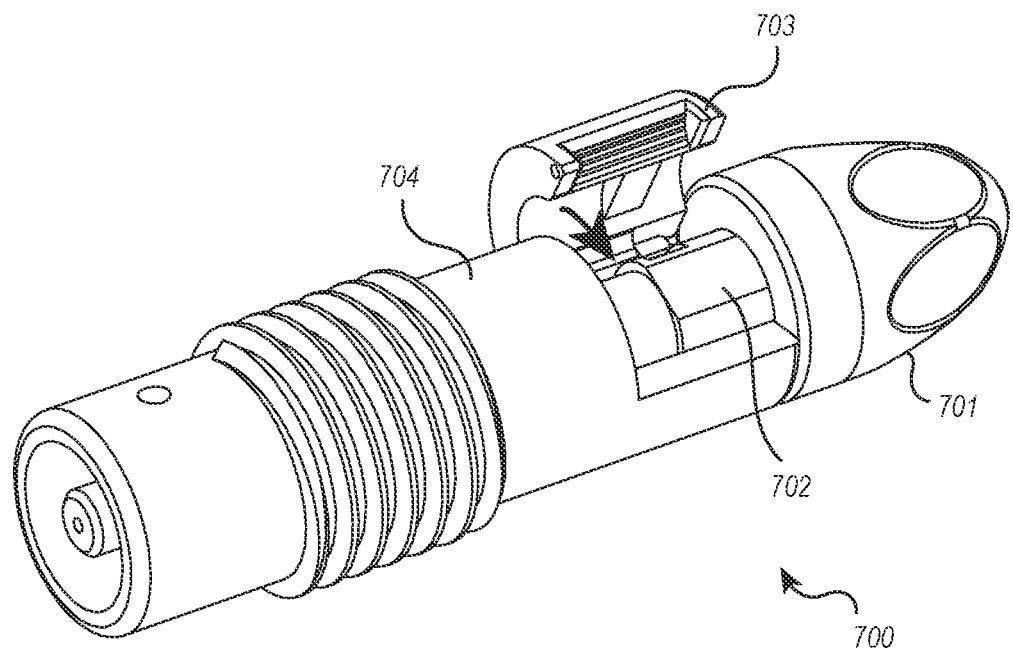
FIG. 22 illustrates in perspective view the deployment system of FIG. 21 in an unlocked configuration.
Figure 23:
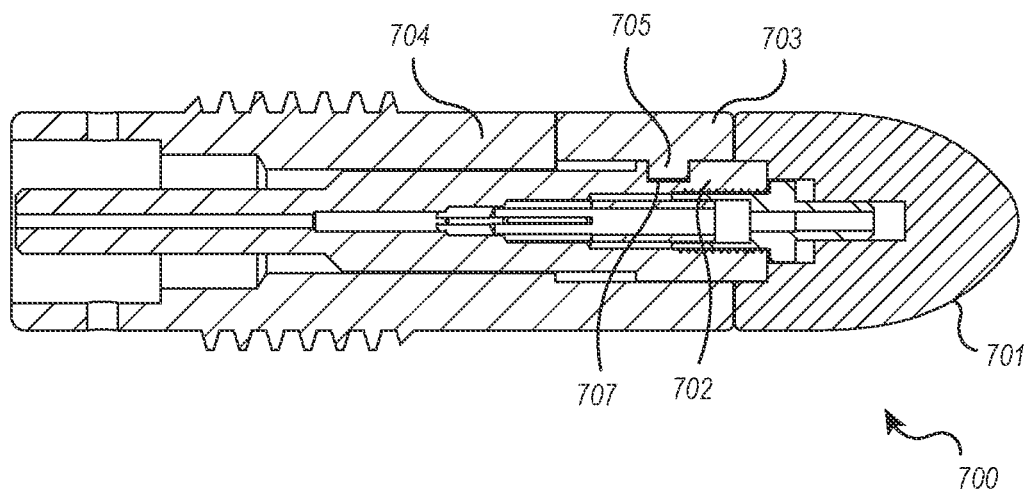
FIG. 23 illustrates in cross-sectional elevational view the deployment system of FIG. 21 in the locked configuration.
Figure 24:
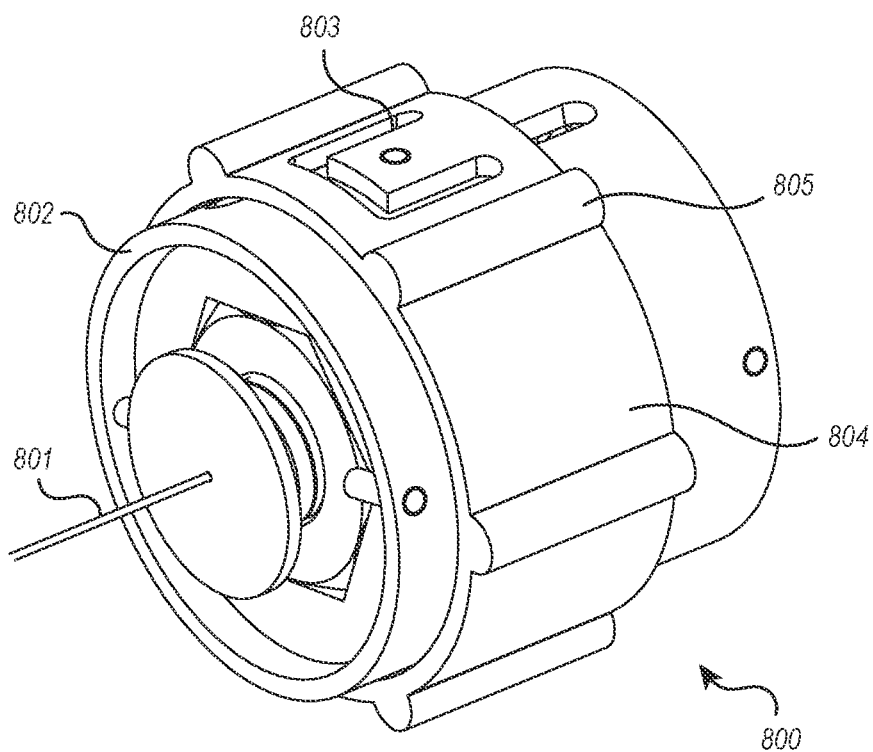
FIG. 24 illustrates in perspective view an embodiment of a deployment system for use with a delivery catheter handle.
Figure 25:
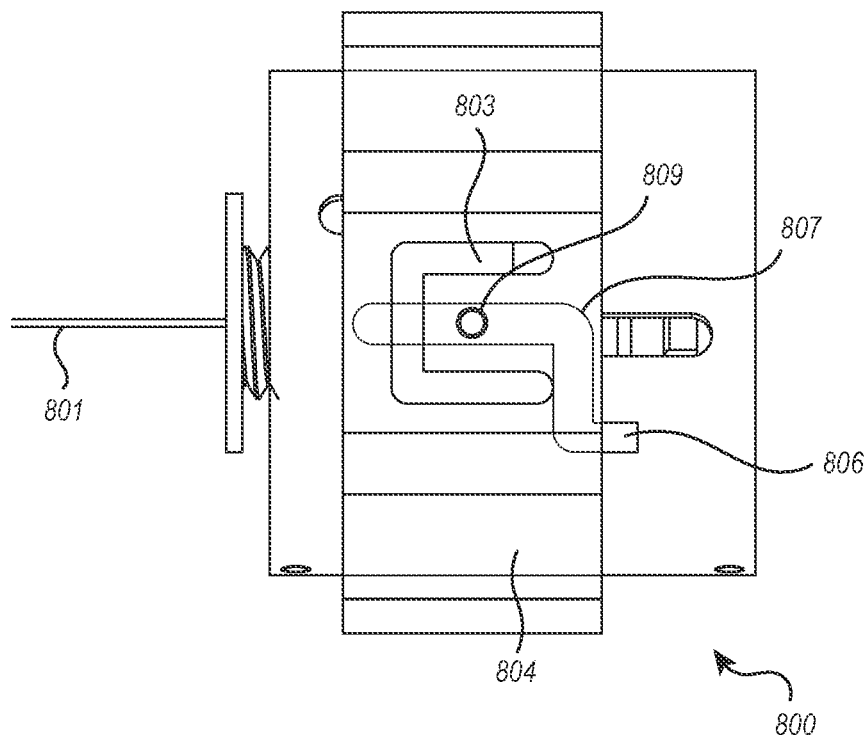
FIG. 25 illustrates in cross-sectional elevational view the deployment system of FIG. 24.
Figure 26:
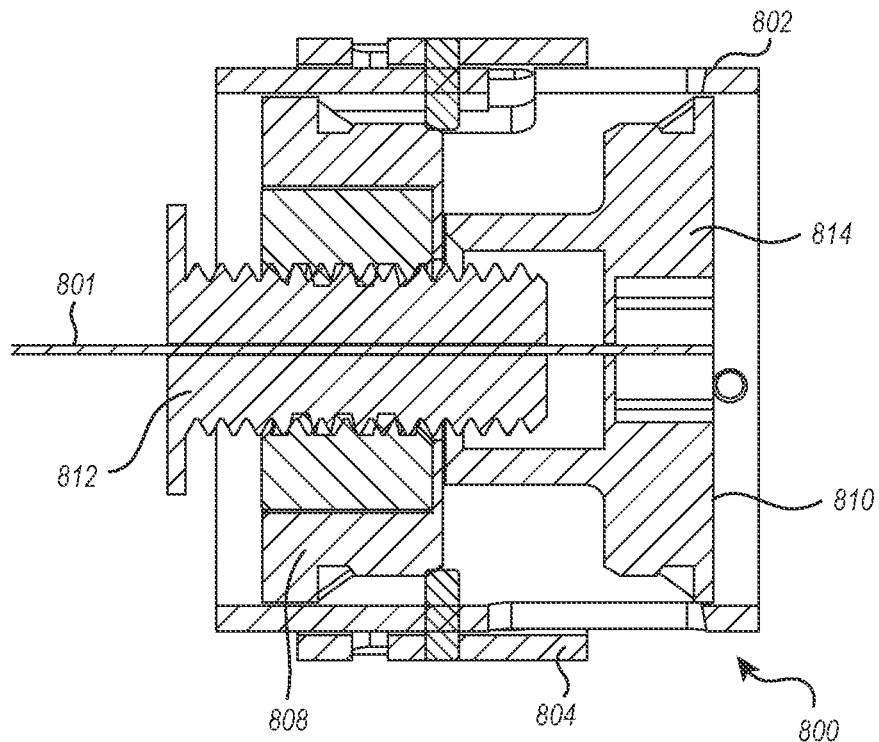
FIG. 26 illustrates in cross-sectional elevational view the deployment system of FIG. 24.
Figure 27:
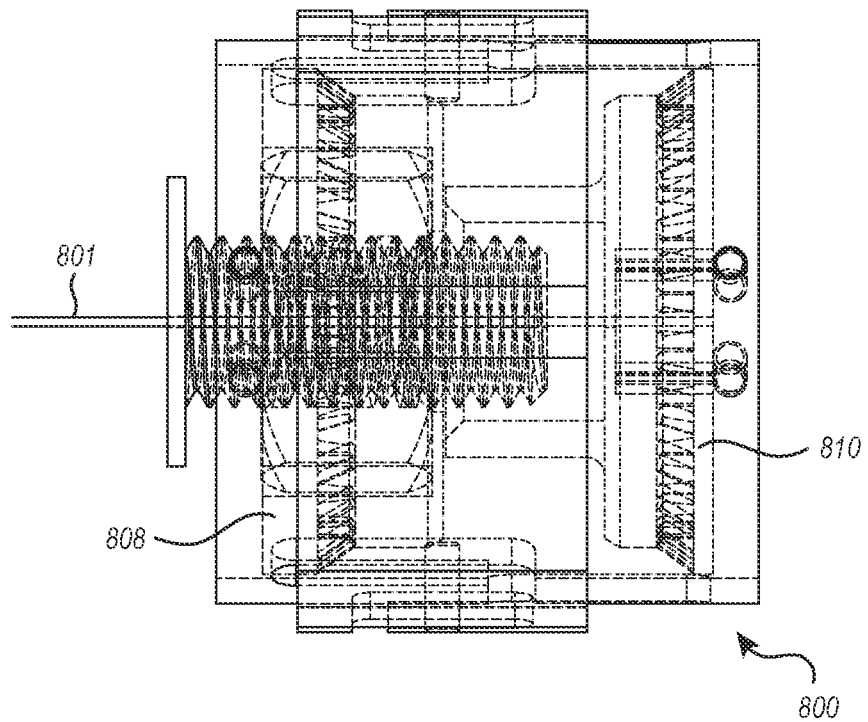
FIG. 27 illustrates in elevational view the deployment system of FIG. 24.

An alternative embodiment of a deployment system according to the disclosure is shown and described regarding FIGS. 21-23. A deployment system 700 may comprise a slider 704 and a cap 701. The slider 704 may comprise an integrated latch or handle 703 that can be toggled between a locked and an unlocked configuration. The latch 703 may advantageously comprise a profile that corresponds to a profile of the slider 704 and thereby minimizes and streamlines the overall size and profile of the system 700.

FIG. 21 shows the latch 703 in the locked configuration, whereas FIG. 22 shows the latch 703 in the unlocked configuration. By lifting the latch 703 up from the slider 704, the crimping cam 702 can be decoupled or unlocked relative to the slider 704, facilitating rotation therebetween and deployment of the fixation device, for example by rotation of the cap 701. In the locked configuration shown in FIG. 23, the locking mechanism of the latch 703 can be seen. A post 705 defined by an inner surface of the latch 703 may cooperate with a recess or detent 707 defined in a surface of the crimping cam 702 to arrest or restrict rotation of the crimping cam 702 relative to the slider 704.

An alternative embodiment of a deployment device according to the disclosure is shown and described regarding FIGS. 24-27. A deployment system 800 may comprise gears housed within an assembly and featuring a control mechanism 804 allowing for independent engagement into each of the gears. The control mechanism 804 may be configured as a ring arranged slidably, translatingly, and/or concentrically on an exterior surface of the assembly 802, through and into which an actuator rod 801 extends and is secured. The control mechanism 804 may comprise ridges or features 805 facilitating accurate transmission of the control mechanism 804 about the assembly 802.

The control mechanism 804 may be formed with a locking mechanism 803 defined through at least part of a thickness of the control mechanism 804 and facilitating selective engagement with gears of the assembly 802. One of the gears may be formed as a slider gear 810 functioning similar to an arm positioner of the previously disclosed embodiments. Another of the gears may be formed as a deployment gear 808 operating to rotate a crimping cam and deploy the fixation device. The control mechanism 804 is selectively engaged with one or the other of the gears, facilitating arm-positioner actuation as well as implant deployment from a single device. This advantageously reduces the number of deployment steps and components while minimizing the cost and complexity of a deployment system.

A cam slot 806 is defined in at least a part of a thickness of the assembly 802 and may allow a practitioner to selectively rotate and translate the control mechanism 804 relative to the outer surface of the assembly 802 along a predetermined path 807. The cam slot 806 may extend in combinations of longitudinal and circumferential directions along the surface of the assembly 802, and particularly may extend between the slider gear 810 and the deployment gear 808. Correspondingly, a cam 809 may be defined an on inner surface of the control mechanism 804 and may travel through the cam slot 806. The cam 809 may be configured to engage a corresponding detent in each of the slider and deployment gears 810, 808.

Actuation of the slider gear 810 by rotation of the control mechanism 804 when the control mechanism 804 is engaged with the slider gear 810 may cause rotation relative to a slider 812, serving to effect translation of the actuation rod 801. Actuation of the deployment gear 808 by rotation of the control mechanism 804 when the control mechanism 804 is engaged with the deployment gear 808 may advantageously result in rotation between the assembly 802 and a crimping cam 814 to cause deployment of the fixation device at the distal end of the actuation rod 801.

Figure 28:
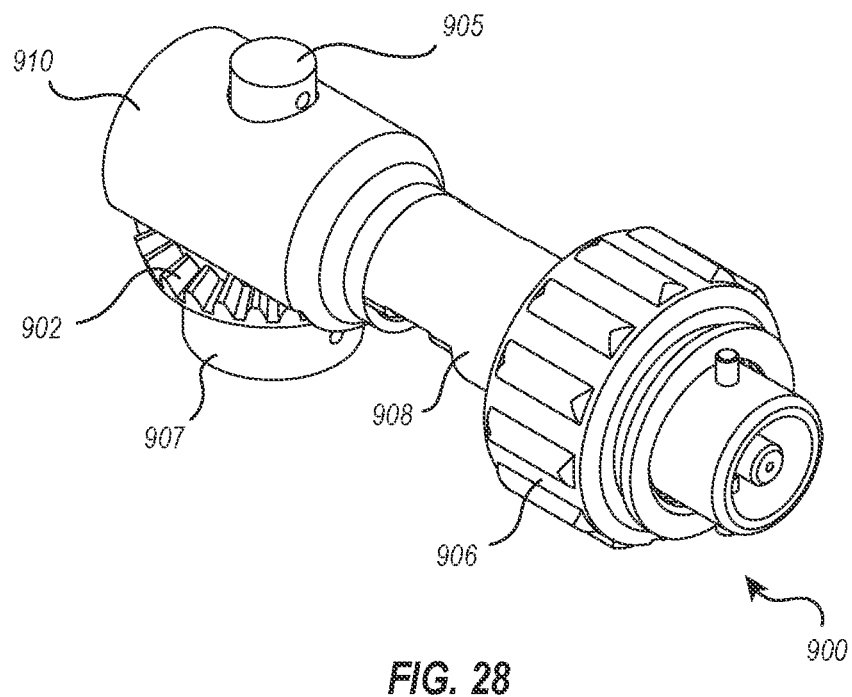
FIG. 28 illustrates in perspective view an embodiment of a deployment system for use with a delivery catheter handle.
Figure 29:
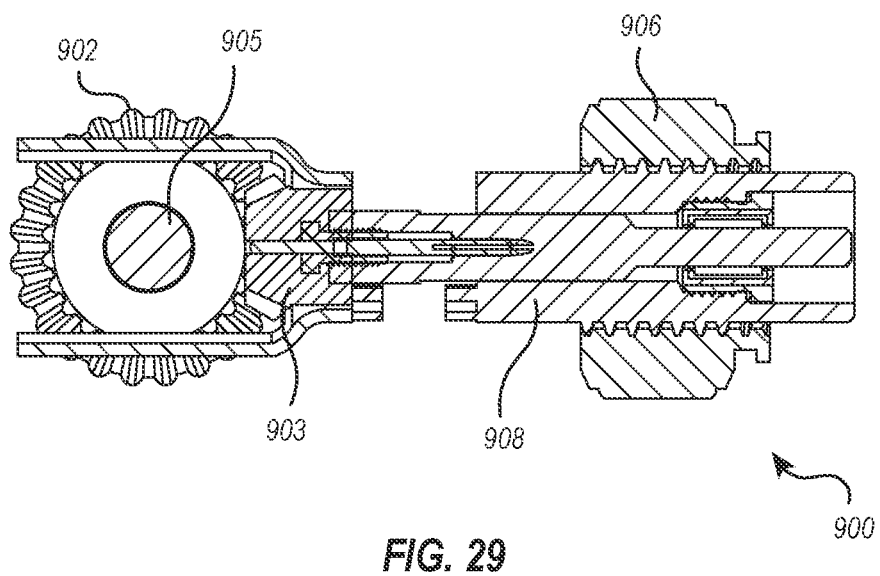
FIG. 29 illustrates in cross-sectional plan view the deployment system of FIG. 28.

An alternative embodiment of a deployment system is depicted and discussed regarding FIGS. 28-29. A deployment system 900 may comprise a bevel gear mechanism 902 attached to the crimping cam 903, with a corresponding knob 907. A post 905 located generally opposite the bevel gear mechanism 902 through and on the housing 910 may secure the bevel gear mechanism 902. An actuator knob 906 may be arranged on an exterior surface of a slider 908, with the crimping cam 903 extending through the slider 908.

The bevel gear mechanism 902 may be configured to reduce a number of input turns from the knob 907 to rotate the crimping cam 903 and thereby deploy the fixation device. This advantageously accelerates the deployment procedure relative to existing devices. To this end, the bevel gear mechanism 902 may have a larger circumference than a circumference of the crimping camp 903. In embodiments, the bevel gear mechanism 902 may have a diameter that is multiple times the diameter of the crimping cam 903. In addition to accelerating the deployment procedure, the size of the bevel gear mechanism may improve ergonomics and ease the use of the deployment system 900, particularly by improving precision of use.

An alternative embodiment of a deployment system is depicted and discussed regarding FIGS. 30-32C. A deployment system 1000 comprises a slider 1002 with a button 1004 located near a proximal end thereof. The button 1004 may be toggled between a locked configuration (shown in FIG. 30) and an unlocked configuration (shown in FIG. 31). The button 1004 may be configured to couple and decouple the slider 1002 from a corresponding crimping cam 1010 by means of a stop component, as discussed in greater detail below. The deployment system 1000 advantageously reduces a profile of the slider 1002 and the deployment system 1000 generally, while also providing for a simple, intuitive, and effective means of facilitating deployment.

Figure 30:
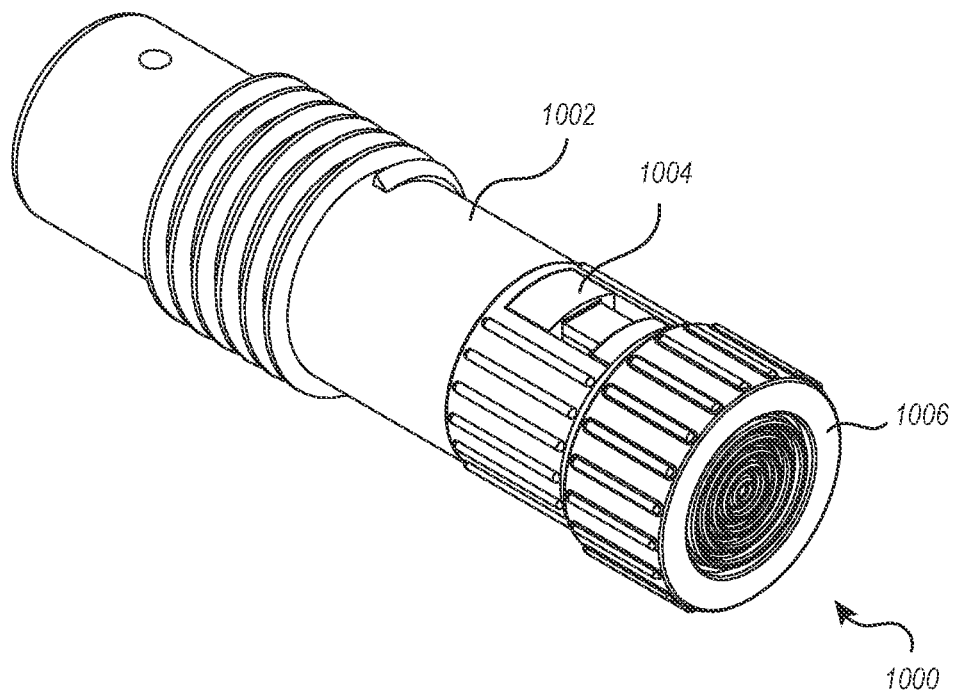
FIG. 30 illustrates in perspective view an embodiment of a deployment system for use with a delivery catheter handle in a locked configuration.
Figure 32A:
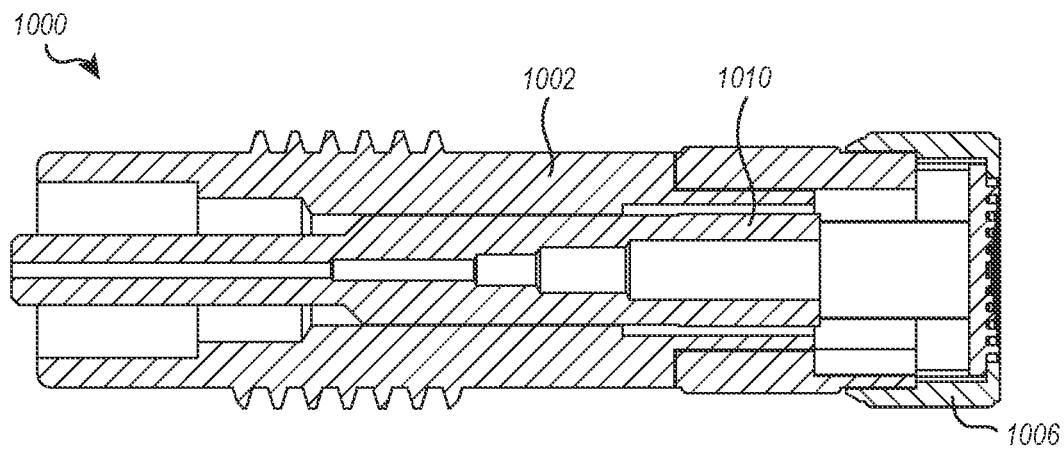
FIG. 32A illustrates in cross-sectional plan view the deployment system of FIG. 30.
Figure 32B:
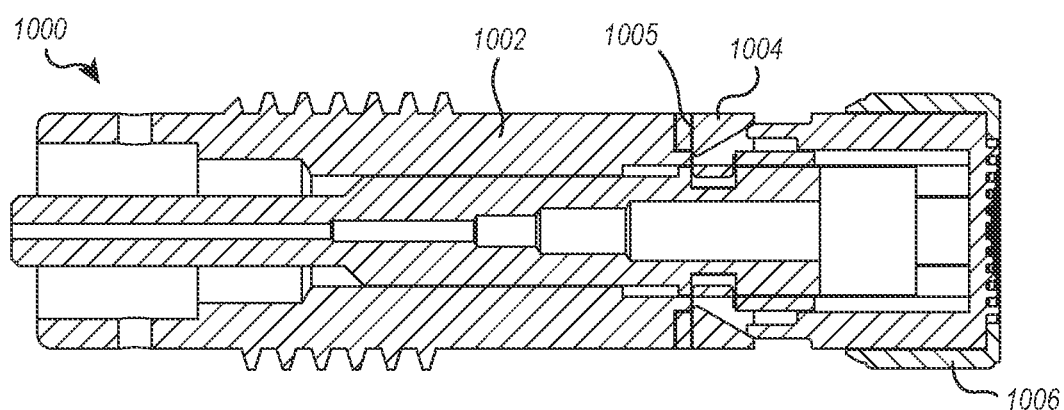
FIG. 32B illustrates in cross-sectional elevational view the deployment system of FIG. 30 in the locked configuration.

In the locked configuration shown in FIG. 30 and FIG. 32B, the button 1004 is "pressed in" or engaged within a recess 1005 defined by the body of the slider 1002. A further recess 1008 may be defined within at least part of a thickness of the crimping cam 1010 and corresponds to a shape of the button 1004. In the locked configuration, the button 1004 couples the slider 1002 and the crimping cam 1010, preventing deployment.

Figure 31:
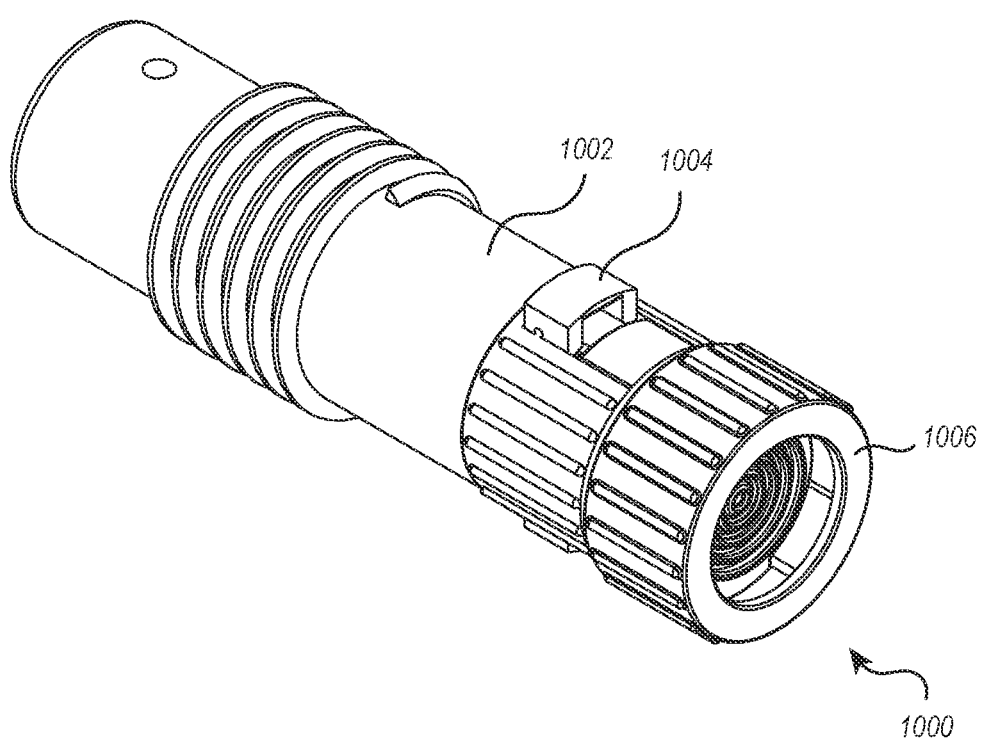
FIG. 31 illustrates in perspective view the deployment system of FIG. 30 in an unlocked configuration.
Figure 32C:
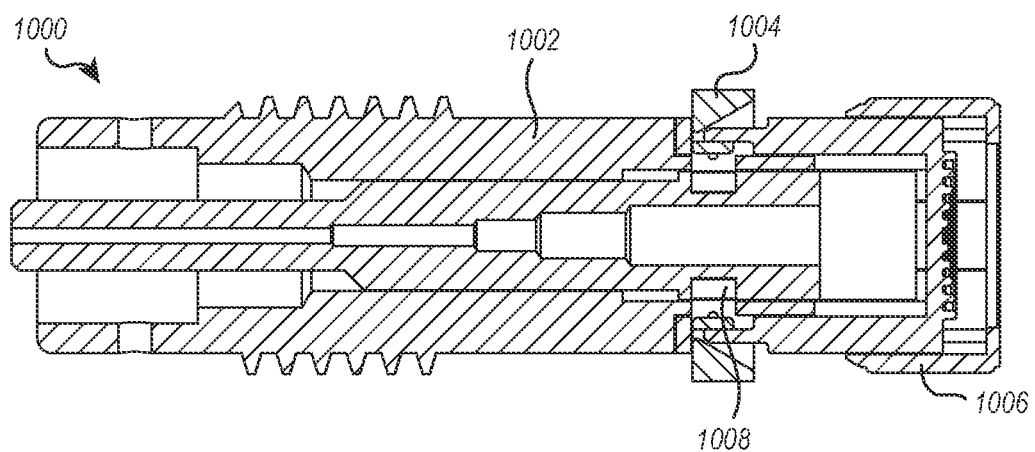
FIG. 32C illustrates in cross-sectional elevational view the deployment system of FIG. 30 in the unlocked configuration.

By contrast, when the button 1004 is in the unlocked configuration shown in FIGS. 31 and 32C, the button 1004 does not couple the crimping cam 1010 and the slider 1002, which allows rotation of the crimping cam 1010 by means of a cap 1006 relative to the slider 1002, which results in deployment of a fixation device.

The deployment system 1000 may provide tension in any suitable manner to generally bias the button 1004 outward, facilitating generally a push-to-eject mechanism. For instance, a resilient component such as a spring (not shown) may be provided in the recess 1005 and/or 1008 to bias the button 1004 outward, with corresponding cam and follower mechanism to either lock the button in the locked configuration or to allow the button to extend to the unlocked configuration based on whether the button has been depressed by a practitioner's finger.

An alternative embodiment of a deployment system according to the disclosure is depicted and discussed regarding FIGS. 33-37. A deployment system 1100 comprises a slider 1112 as described in regard to the aforementioned embodiments. Deployment of a fixation device is either allowed or prevented by a shield component 1106 extending from the slider 1112 and restricting access generally to a knob 1102 used for rotating a crimping cam 1114 relative to the slider 1112.

Figure 33:
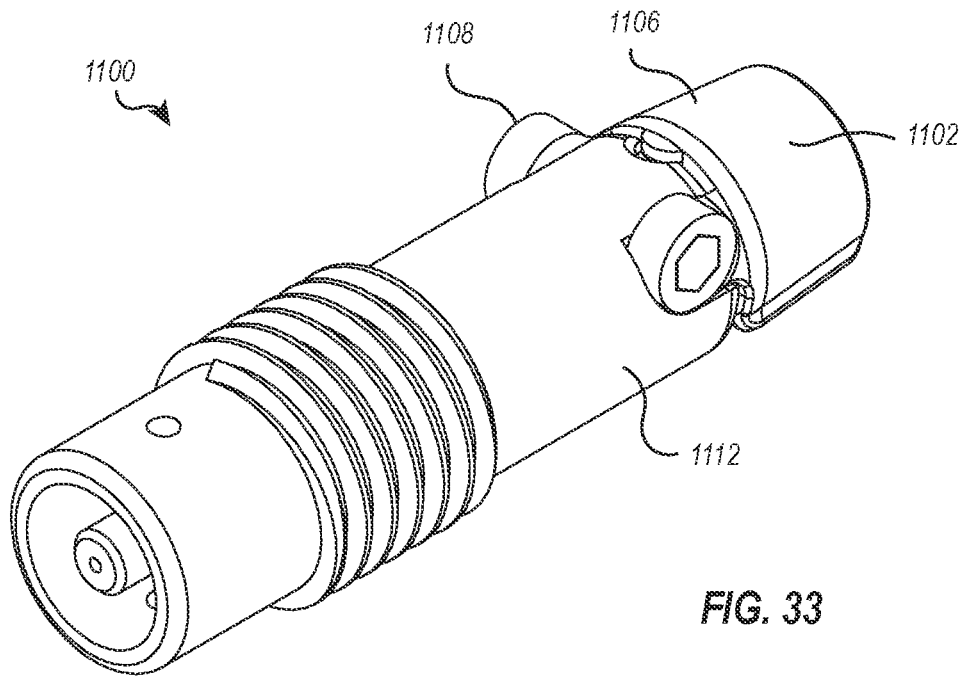
FIG. 33 illustrates in perspective view an embodiment of a deployment system for use with a delivery catheter handle in a locked configuration.
Figure 35:
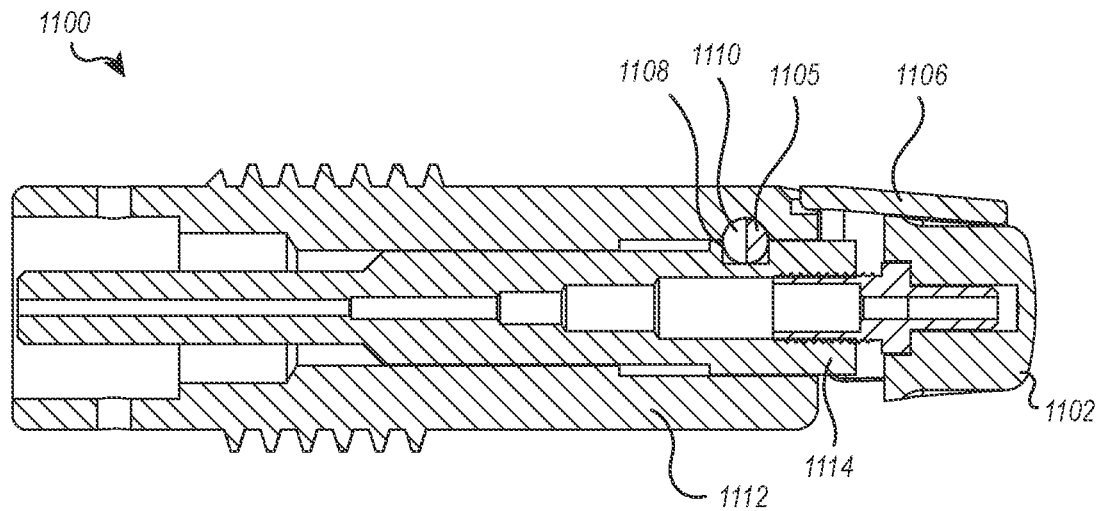
FIG. 35 illustrates in cross-sectional elevational view the deployment system of FIG. 33 in the locked configuration.

The shield component 1106 may have a profile 1107 generally corresponding to a shape of the slider 1112, i.e. a curved profile, such that the shield component 1106 extends generally continuously with at least a portion of the slider 1112 in a locked configuration, as shown in FIGS. 33 and 35. The shield component 1106 may likewise be formed of a same material as the material defining the slider 1112.

Figure 34:
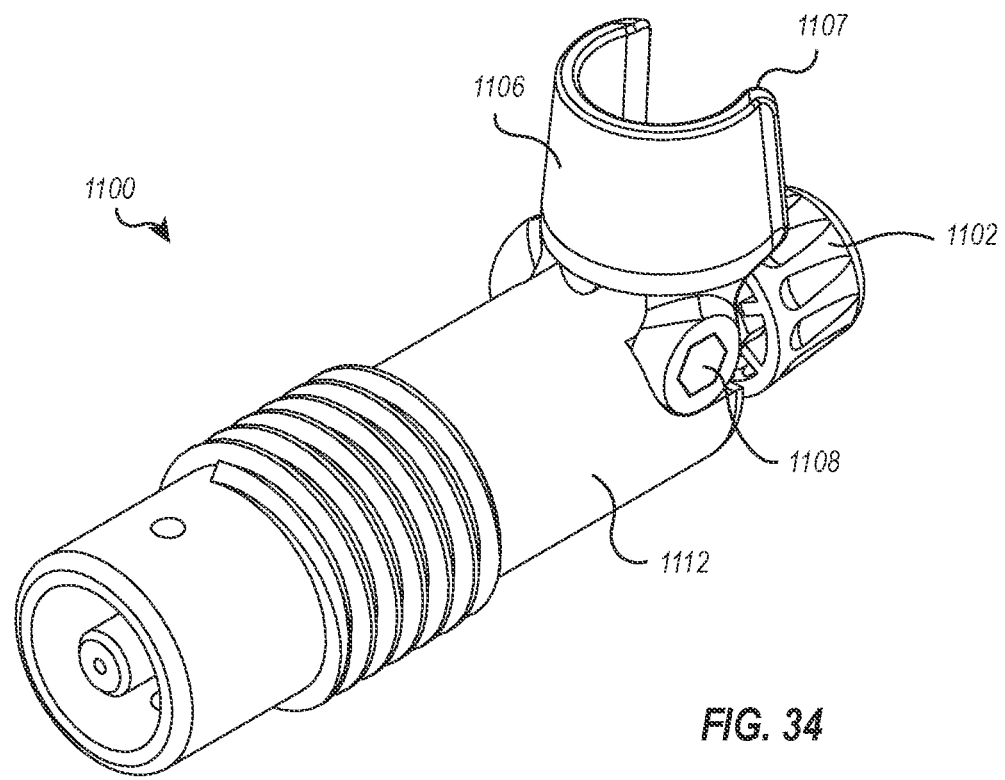
FIG. 34 illustrates in perspective view the deployment system of FIG. 33 in an unlocked configuration.
Figure 36:
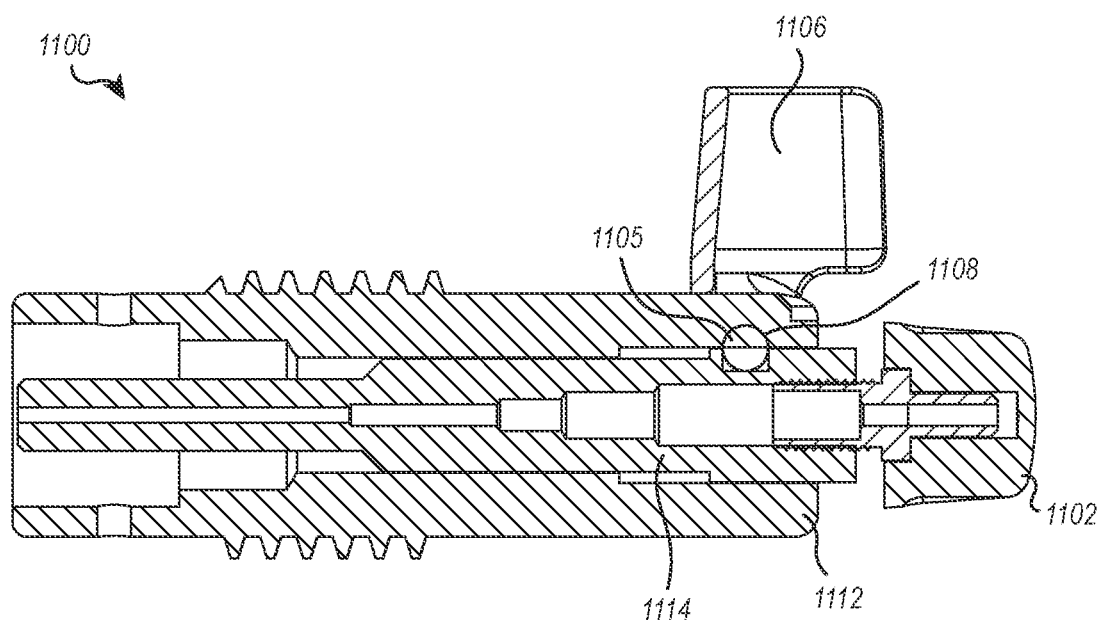
FIG. 36 illustrates in cross-sectional elevational view the deployment system of FIG. 33 in the unlocked configuration.
Figure 37:
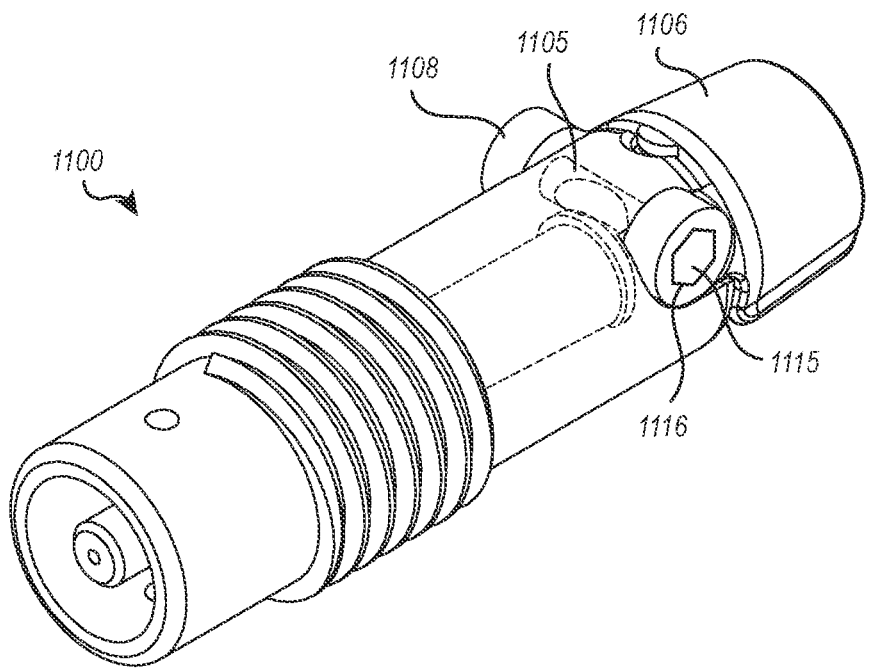
FIG. 37 illustrates in perspective view the deployment system of FIG. 33 in the locked configuration.
Figure 38:
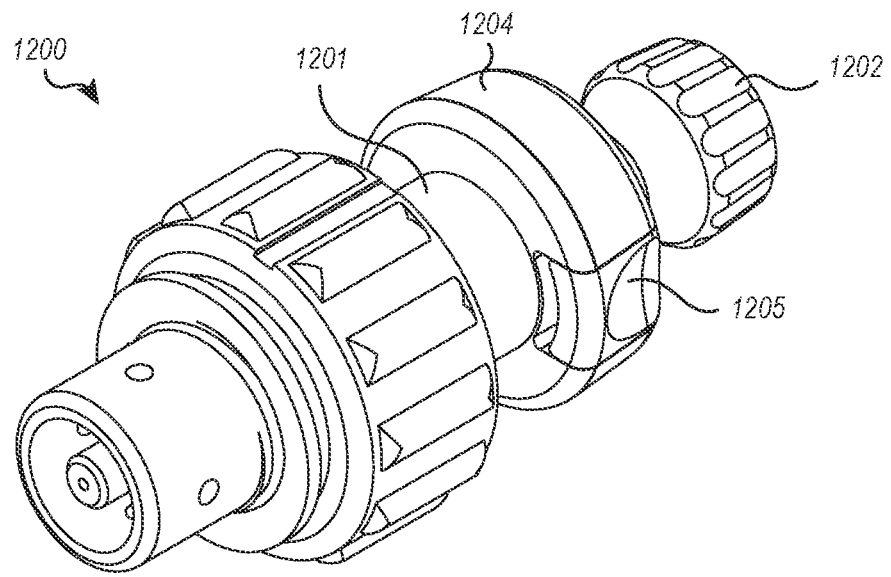
FIG. 38 illustrates in perspective view an embodiment of a deployment system for use with a delivery catheter handle.
Figure 39:
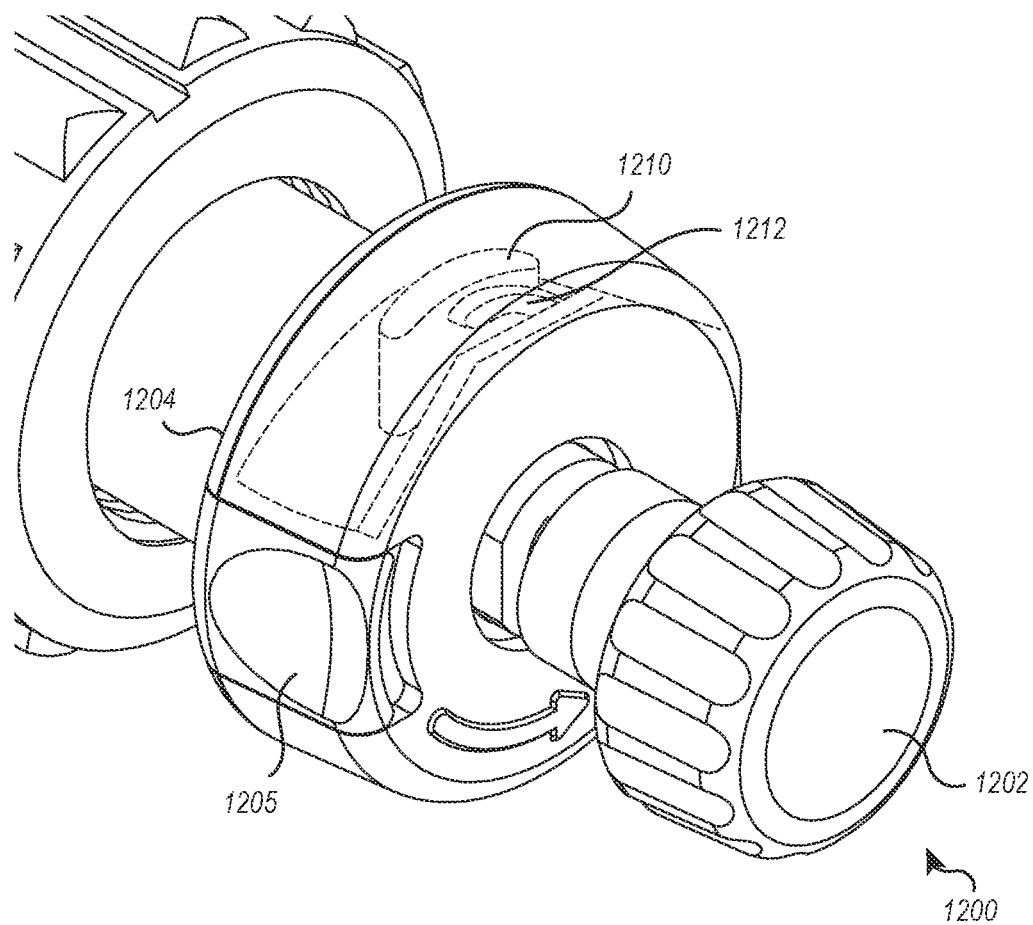
FIG. 39 illustrates in perspective view the deployment system of FIG. 38.

By contrast, in an unlocked configuration as depicted in FIGS. 34 and 36, the shield component 1106 may pivot or rotate to an extended configuration substantially at a right angle with a surface of the slider 1112. The shield component 1106 may pivot about a hinge 1108 defined in a thickness of the slider 1112. The hinge 1108 may comprise a pin component 1105 that engages corresponding bearings defined by the slider 1112, for example in a channel 1110 extending through the slider 1112 body.

The pin component 1105 in embodiments may be formed as a "half pin" or with a semi-circular cross-section. In embodiments, the pin component 1105 may cooperate with the channel 1110 to form a stop at the upright position shown in FIGS. 34 and 36. Additionally or alternatively, the pin component 1105 and the channel 1110 may cooperate to bias the shield component 1106 towards the locked configuration. In embodiments, the pin component 1105 may comprise expanded end portions 1115 extending outside of a body of the slider 1112 and facilitating secure engagement with and rotation relative to the slider 1112. In embodiments, the pin component 1105 may require the use of a tool shaped to correspond to an aperture 1116 defined in the end portions 1115 for rotating the shield component 1106, further reducing the risk of unintentional rotation.

An alternative embodiment of a deployment system is depicted and discussed in regard to FIGS. 38-41. A deployment system 1200 may comprise a slider 1201 and a corresponding crimping cam 1203, with a knob 1202 arranged to facilitate rotation between the crimping cam 1203 and the slider 1201 to deploy a fixation device.

A wedge component 1210 may lock rotation of the crimping cam 1203 by the knob 1202 relative to the slider 1201 by extending into a recess 1209 defined by a surface of the crimping cam 1203. The wedge component 1210 may comprise any suitable material. In embodiments, the wedge component 1210 may have sufficient strength and/or rigidity to resist torque applied by the knob 1202.

The wedge component 1210 may be controlled relative to the crimping cam 1203 by an outer ring 1204 extending concentrically about the slider 1201 and over the wedge component 1210. The outer ring 1204 may define within a thickness of the outer ring 1204 a cam slot 1212 corresponding to a cam 1211 defined on and/or by the wedge component 1210.

The cam slot 1212 may extend circumferentially about the ring 1204 in a path that, as the outer ring 1204 is rotated relative to the slider 1201 by a predetermined amount, the wedge component 1210 is depressed into the recess 1209 or out of the recess 1209. In embodiments, the cam slot 1212 may progressively extend closer to an outer diameter of the outer ring to draw the wedge component 1210 out, and may progressively extend closer to an inner diameter of the outer ring to depress the wedge component 1210.

Figure 40:
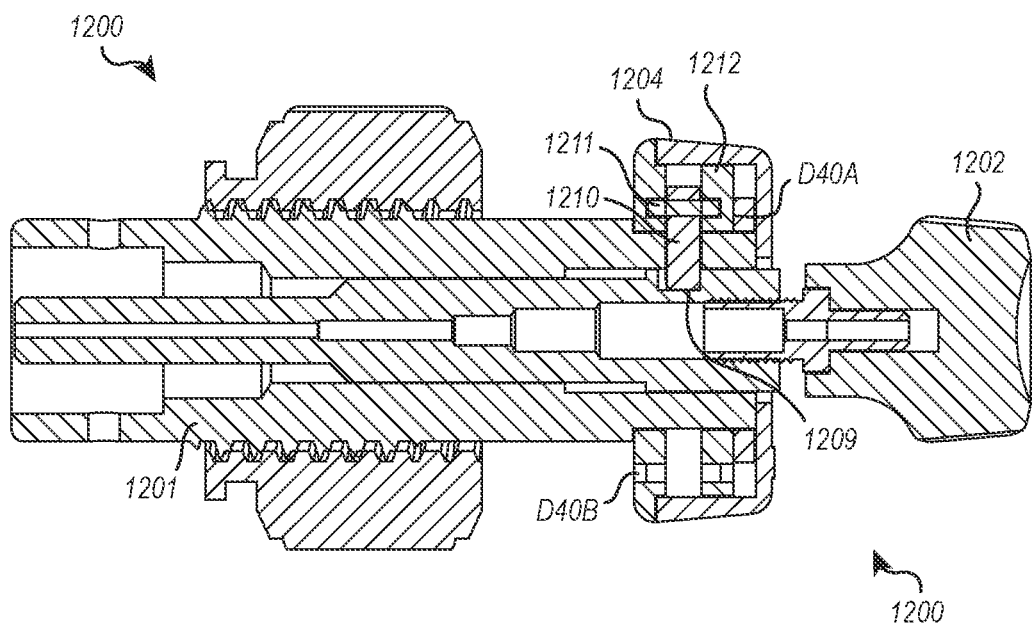
FIG. 40 illustrates in cross-sectional elevational view the deployment system of FIG. 38 in a locked configuration.

As seen in FIG. 40, a distance D40A between the cam slot 1212 and the slider 1201 corresponding to the locked configuration may be lower than a distance D40B between the cam slot 1212 and the slider 1201 corresponding to the unlocked configuration. In embodiments, the ring 1204 may be rotated by approximately 180° to withdraw the wedge component 1210 from the locked configuration.

A button 1205 may be provided on a portion of the outer diameter of the ring 1204. The button 1205 may, when depressed by a practitioner during gripping of the ring 1204, facilitate rotation, whereas when the button 1205 is not depressed, the ring 1204 is not able to rotate. The button 1205 may utilize any suitable means for locking and unlocking rotation, including a resilient or tensioning element configured to selectively apply friction against a surface of the slider 1201. In embodiments, two buttons may be provided on opposed sides of the outer ring 1204 to facilitate gripping and rotating on both sides by the practitioner.

Figure 41:
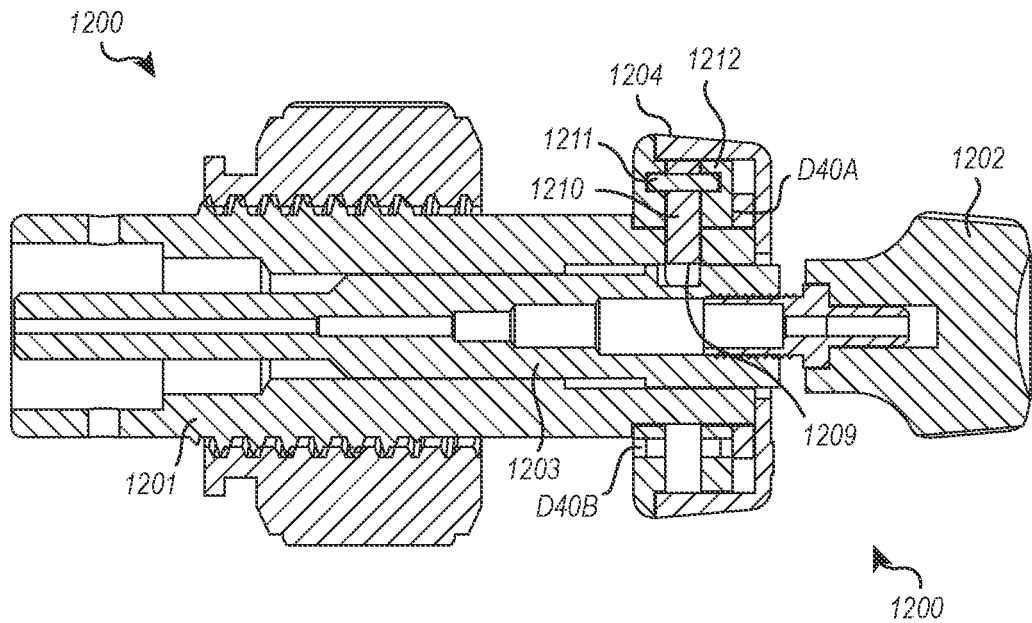
FIG. 41 illustrates in cross-sectional elevational view the deployment system of FIG. 38 in an unlocked configuration.

When the wedge component 1210 is withdrawn from the recess 1209 as shown in FIG. 41, the knob 1202 may be rotated by a practitioner to rotate the crimping cam 1203 relative to the slider 1201, resulting in deployment of the fixation device. The embodiment of FIGS. 39-41 advantageously provides a simple, effective, and intuitive system for controlled deployment of a fixation device.

Figure 42:
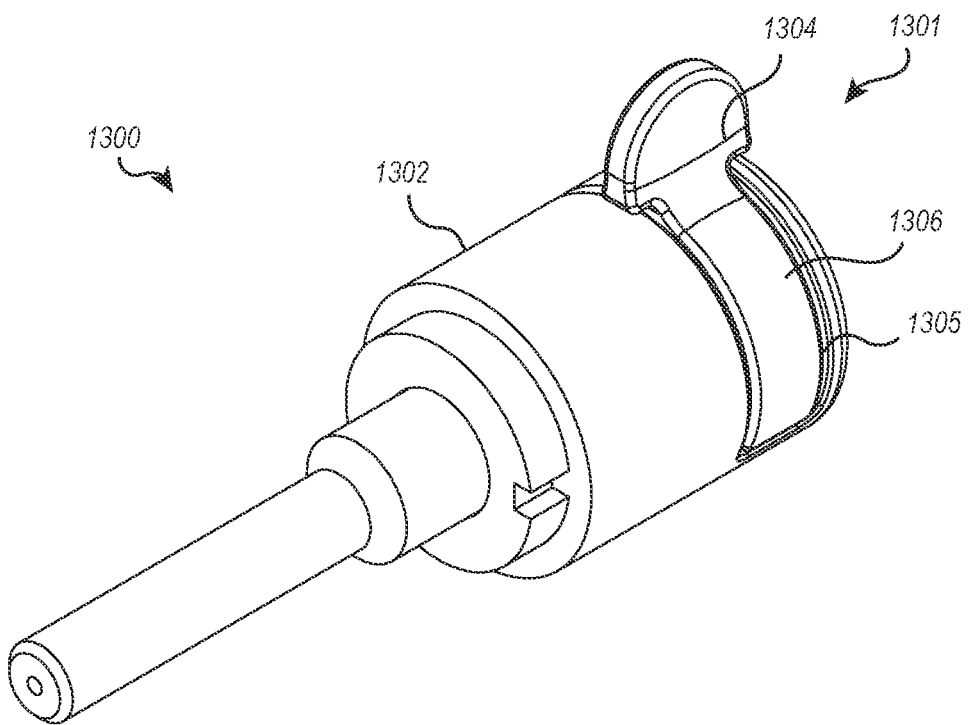
FIG. 42 illustrates in perspective view an embodiment of a deployment system for use with a delivery catheter handle.
Figure 43:
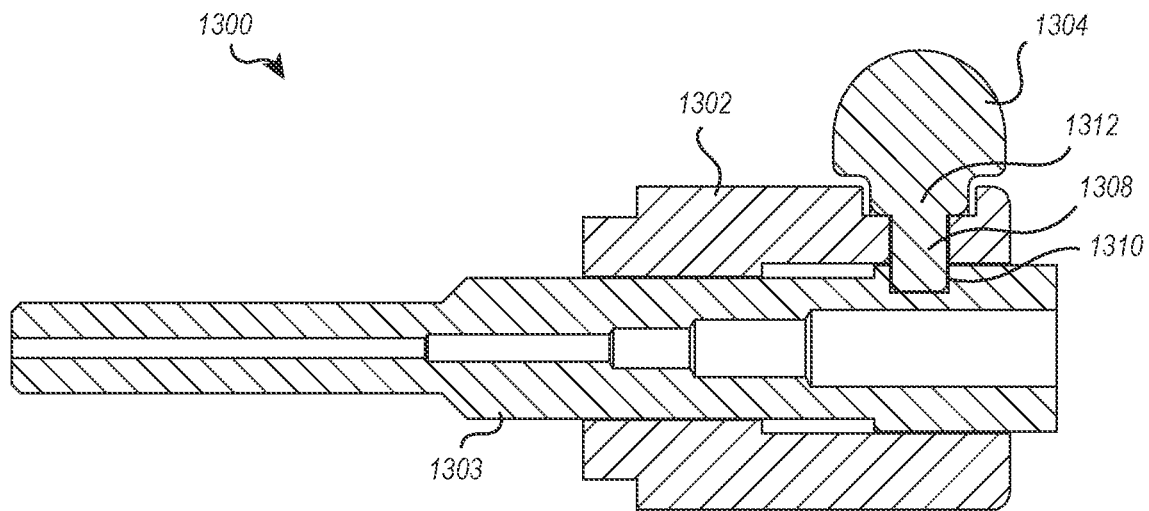
FIG. 43 illustrates in cross-sectional elevational view the deployment system of FIG. 42.

In an alternative embodiment depicted in FIGS. 42 and 43, a deployment system 1300 comprises a slider 1302 on which a pin and slot mechanism 1301 operates to couple the slider 1302 and a crimping cam together, preventing deployment until the pin and slot mechanism 1301 is released. The pin and slot mechanism 1301 may comprise a handle 1304 that extends beyond a surface of the slider 1302 and an arm 1306 that extends within a recess 1305 defined through at least a portion of a thickness of the slider 1302. The recess 1305 may be configured such that the arm 1306 is generally continuous or coextensive with the surface of the 1302 and does not extend beyond the surface.

The handle 1304 may comprise or be connected to a main body portion 1312 of the pin and slot mechanism 1301 and a pin 1308. The pin 1308 may extend through the slider 1302 into a thickness of the crimping cam 1303. The crimping cam 1303 may define a recess 1310 configured to receive the pin 1308, which, when engaged therewith, arrests or restricts rotation of the crimping cam relative to the slider 1302. The handle 1304, the main body portion 1312, and the pin 1308 may be formed of any suitable material. In embodiments, the pin 1308 may be sufficiently rigid or strong to resist torque applied by a knob (not shown) of the deployment system 1300. In embodiments, the arm 1306 may attach at a terminal end to a hinge that allows the pin and slot mechanism 1301 to pivot and to be replaceable relative to the deployment system 1300. In other embodiments, the pin and slot mechanism 1301 is configured for a single use and is discardable.

Figure 44:
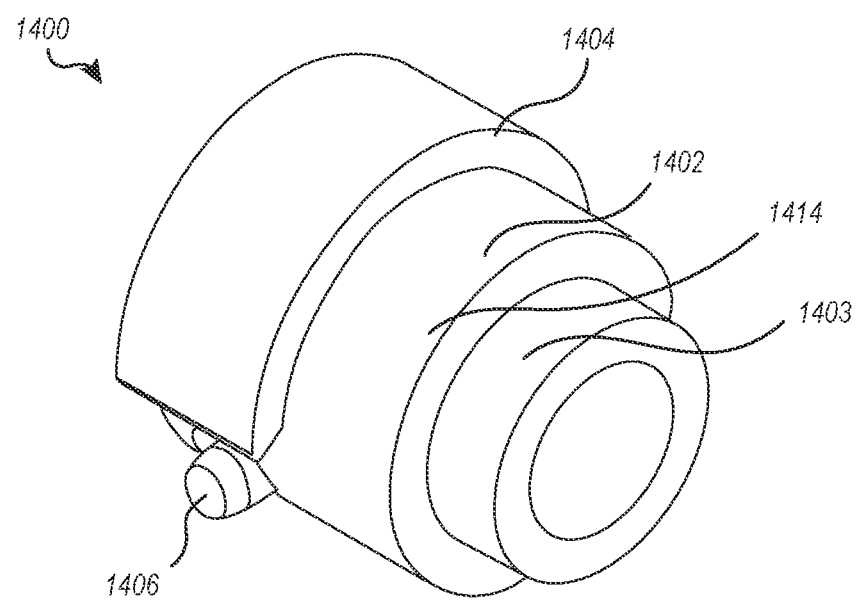
FIG. 44 illustrates in perspective view an embodiment of a deployment system for use with a delivery catheter handle in a locked configuration.
Figure 45:
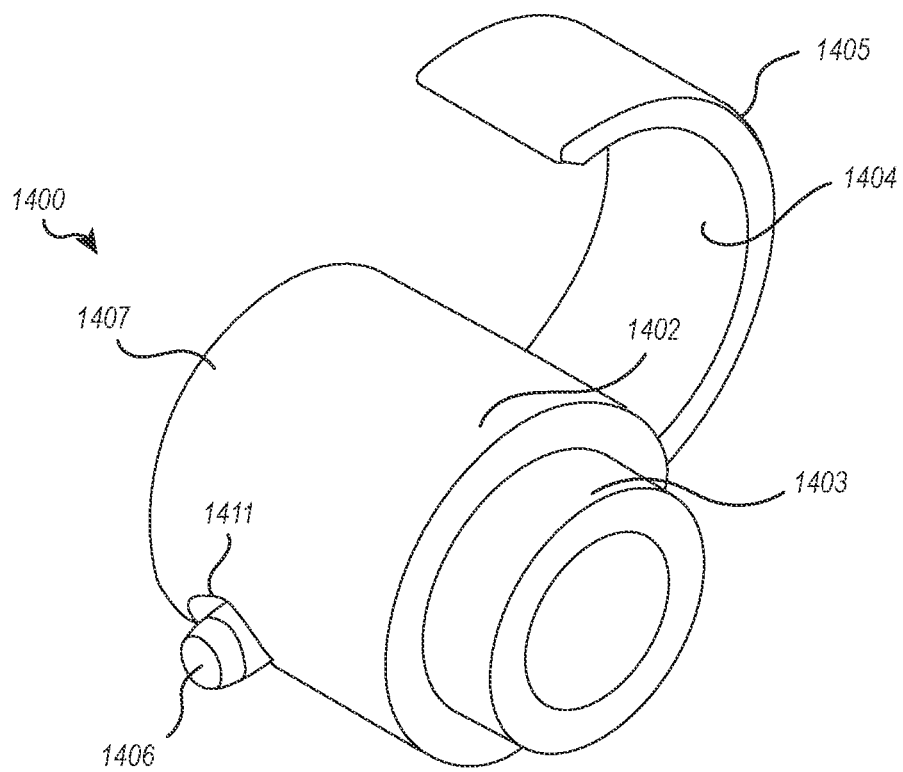
FIG. 45 illustrates in perspective view the deployment system of FIG. 44 in an unlocked configuration.
Figure 46:
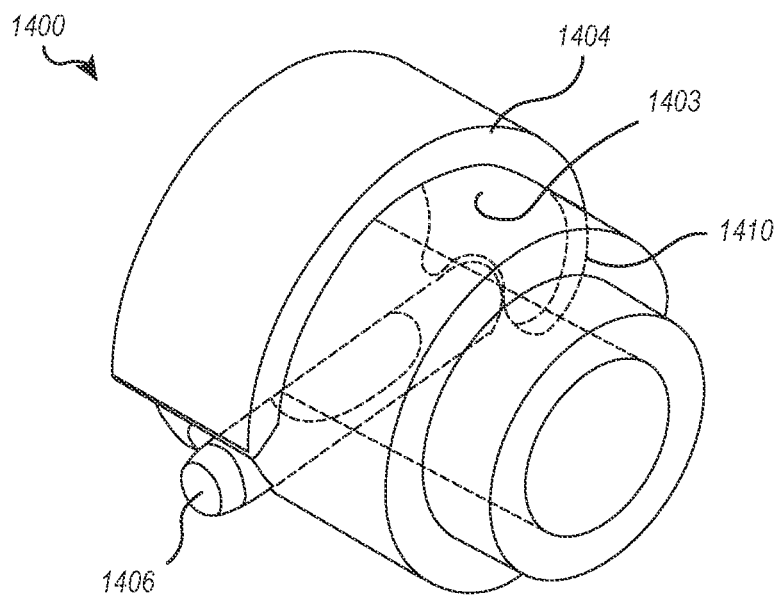
FIG. 46 illustrates in perspective view the deployment system of FIG. 44 in the locked configuration.

In an alternative embodiment of a deployment system depicted and discussed in regard to FIGS. 44-46, a deployment system 1400 comprises a slider 1402 and a handle 1404 arranged to sit substantially flush with the slider 1402 in a locked configuration. That is, the slider 1402 and the handle 1404 may be arranged in a substantially concentric arrangement to maintain a minimized profile. The handle 1404 may be pivotable relative to the slider 1402 so as to pivot between a locked configuration (shown in FIGS. 44 and 46) and an unlocked configuration (shown in FIG. 45). In the depicted embodiment, the handle 1404 may extend around a portion of the slider 1402, e.g. about substantially one half of the slider 1402.

The handle 1404 may comprise a curved profile 1405 that corresponds to a curved profile 1407 of the slider 1402, which advantageously minimizes a profile of the deployment system 1400 in the engaged configuration, particularly compared to existing deployment systems which often comprise a pin extending generally transversely to the slider and substantially beyond the outer diameter thereof.

The handle 1404 may engage a deployment pin 1406 that extends through a thickness of the slider 1402, as seen in FIG. 46. The deployment pin 1406 may lock rotation of the slider 1402 relative to an internally disposed crimping cam 1403. In embodiments, the deployment pin 1406 may extend through a channel 1411 defined at an interior of both the slider 1402 and the crimping cam 1403.

The handle 1404 may connect to and manipulate the deployment pin 1406 via a hinge 1410. The hinge 1410 may be configured to permit removal of the pin 1406 when the handle 1404 is rotated to the unlocked configuration shown in FIG. 45 and to prevent removal of the pin 1406 when the handle 1404 is in the locked configuration of FIGS. 44 and 46. To remove the deployment pin 1406, for example, the handle 1404 and the deployment pin 1406 may be pulled away and detached from the slider 1402. The shape and configuration of the handle 1404 may advantageously provide additional leverage to pull the deployment pin 1406 from the slider 1402 and the crimping cam 1403.

The arrangement of the deployment system 1400 advantageously provides a deployment pin 1406 for controlling deployment of a fixation device by allowing a practitioner to easily, intuitively, and effectively lock and unlock rotation of the slider 1402 and crimping cam 1403 while reducing the profile of the deployment system 1400.

Figure 47:
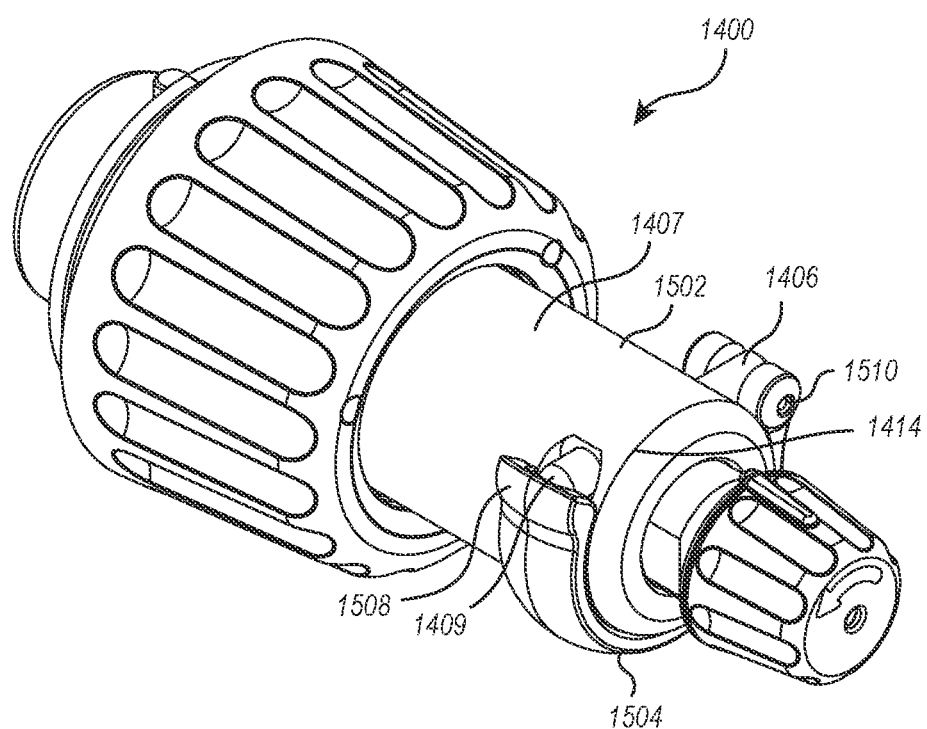
FIG. 47 illustrates in perspective view the deployment system of FIG. 44 with another embodiment of a delivery catheter handle in a locked configuration.
Figure 48:
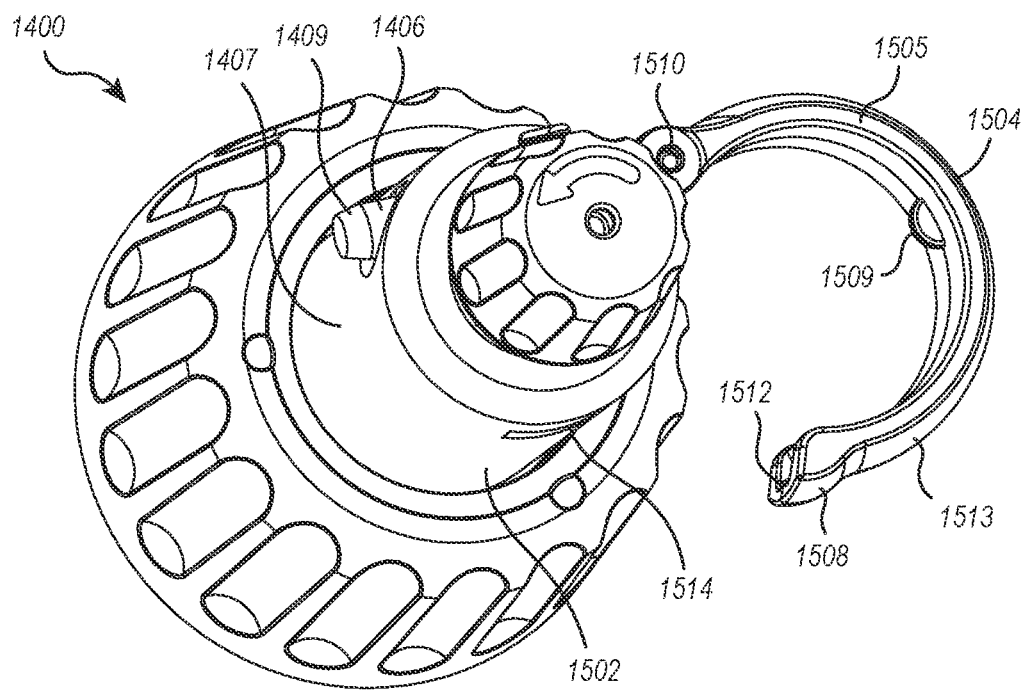
FIG. 48 illustrates in perspective view the deployment system of FIG. 47 with the delivery catheter handle in an unlocked configuration.
Figure 49:
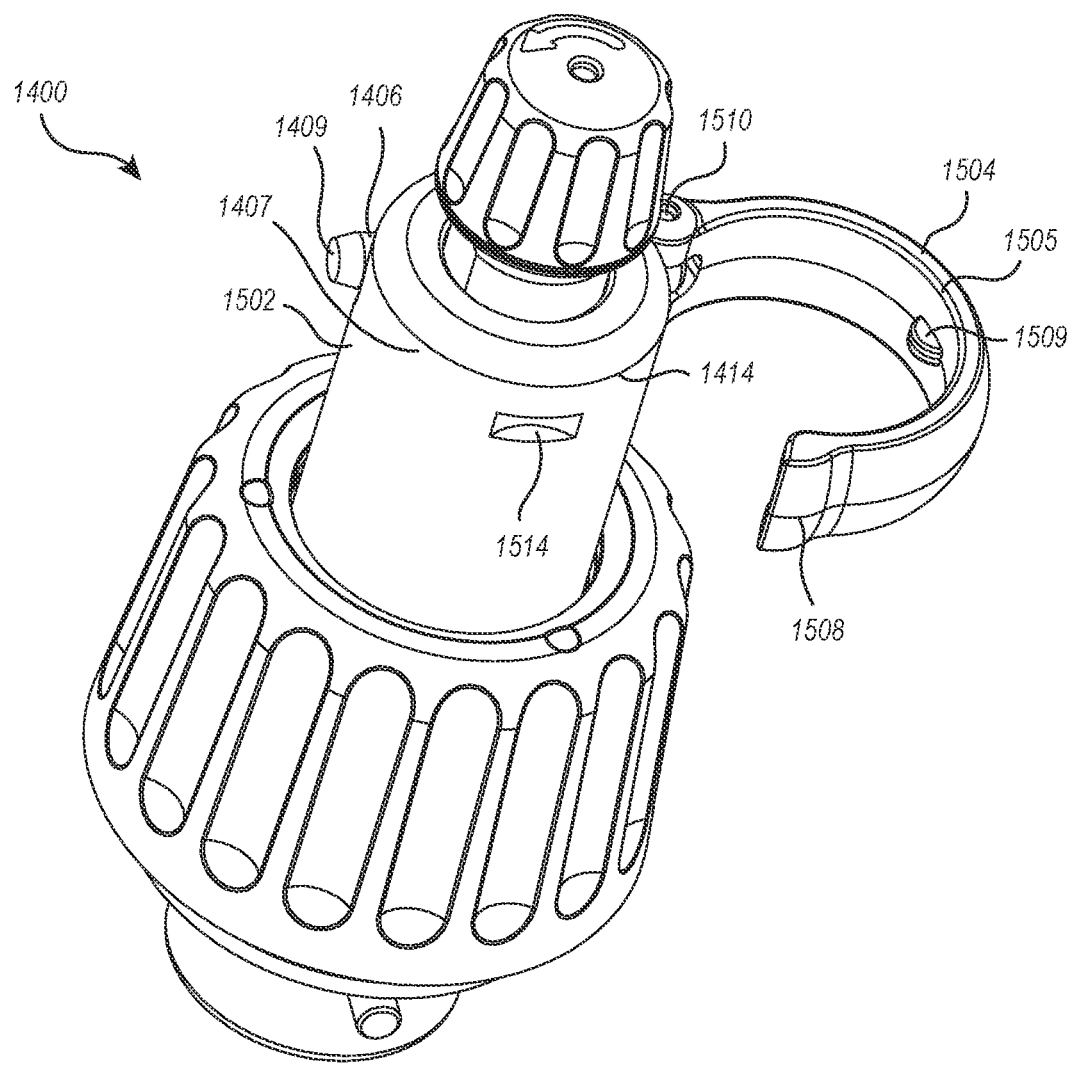
FIG. 49 illustrates in perspective view the deployment system of FIG. 47 with the delivery catheter handle in an unlocked configuration.

FIGS. 47-49 illustrate another embodiment of deployment system 1400, wherein the handle 1504 is configured to latch on to or snap into place around the slider 1502. The handle 1504 can have a curvature 1505 that is complementary to the circumference or curved profile 1407 of the slider 1502. The curvature 1505 can be associated with an interior surface 1516 of the handle 1504. An outer surface 1513 of the handle 1504 can have the same curvature 1505 or some other curvature. Additionally, the curvature 1505 can be uniform along the length of the interior surface 1516 or include a plurality of discrete portions that collectively form the curvature 1505.

The handle 1504 may connect to the deployment pin 1406 via a hinge 1510. The hinge 1510 may be configured to allow movement of the handle 1504 in relation to the pin 1406 and to disengage the handle 1504 from the slider 1502. This permits removal of the pin 1406 when the handle 1504 is rotated to the unlocked configuration, as shown in FIGS. 48 and 49, and to prevent removal of the pin 1406 when the handle 1504 is in the locked configuration of FIG. 47. The handle 1504 can be used to manipulate the deployment pin 1406 to allow rotation and/or sliding movement of the pin 1406 in relation to the slider 1502. The handle 1504 can be sized and configured to span at least a majority of the circumference of the slider 1502 (or the curved profile 1407 of the slider 1502) when the handle 1504 is in a locked configuration. By spanning at least, a majority of the circumference of the slider 1502, the handle 1504 may be enabled to maintain the locked configuration.

The handle 1504, as shown in the figures, includes a pin cover 1508. The pin cover 1508 can be configured to cover and retain the pin tip 1409 when the handle 1504 is in the locked configuration, which can in turn retain the pin 1406 within the channel 1411. The pin cover 1508 can have a groove 1512 which can provide a space for the pin tip 1409. This prevents inadvertent contact with the pin 1406 that could result in premature disengagement of the pin 1406 because the impact on the pin 1406 is sufficient to overcome the engagement between the handle 1504 and the slider 1502.

The handle 1504 can also include at least one protuberance 1509 on the interior surface 1516 of the handle 1504 that cooperates with an indentation or notch 1514 in the slider 1402. The protuberance 1509, as shown in FIGS. 48 and 49 has a semi-circular shape, though it will be understood that the protuberance 1509 can be formed in a variety of shapes, such as portions of a polygon, oval, combinations and/or modification thereof, or other shape that allows for slidable engagement between the protuberance and the indentation or notch 514 in the slider 1402. The notch 1514 can be located on the slider 1402 so that the protuberance 1509 is inserted into the notch 1514 when the handle 1504 is in the locked configuration. The notch 1514 can complement the shape of the protuberance 1509. The protuberance 1509 and notch 1514 can prevent the handle 1504 from rotating off of the distal end 1414 of the slider 1402.

It will be understood that the disclosed deployment system embodiments are merely exemplary, and that any suitable material, configuration, mechanism, or other feature may be used in combination with one or more features or one or more of the above embodiments according to and within the spirit and scope of the disclosure. In addition, the disclosed embodiments are not limited to mitral valve-related treatments or medical treatments and devices generally but rather extend to any suitable device, system, or method.

By providing a locking system according to embodiments of the current disclosure, the problem of existing delivery catheter handles being unreliable or difficult to use, particularly for locking translation of the delivery catheter relative to the handle, is addressed. In particular, embodiments of the disclosure allow for an improved, intuitive, and effective system for locking translation and/or deployment by a practitioner.

By providing a deployment system according to embodiments of the current disclosure, the problem of existing deployment systems having undesirable profiles and being unintuitive to use is addressed. The disclosed embodiments allow for an improved, simple, low-profile, and intuitive deployment system for effectively locking deployment and/or translation of the device.

Following are some further example embodiments of the invention. These are presented only by way of example and are not intended to limit the scope of the invention in any way.

Embodiment 1. A deployment system for a fixation device, the deployment system including a slider component defining a slider track on an outer surface thereof, a crimping cam slidably arranged within and concentric with the slider component, and a locking component.

Embodiment 2. The deployment system of Embodiment 1, wherein the locking component comprises a ring rotatably arranged on the outer surface of the slider component, the ring component defining a cam on an inner diameter thereof.

Embodiment 3. The deployment systems of any of Embodiments 1-2, wherein the cam is configured to cooperate with the slider track, the slider track extending between a first end corresponding to an unlocked configuration and a second end corresponding to a locked configuration.

Embodiment 4. The deployment system of any of Embodiments 1-3, wherein in the locked configuration the cam couples the slider component and the crimping cam, preventing rotation therebetween.

Embodiment 5. The deployment system of any of Embodiments 1-4, further comprising a cap operably connected with the crimping cam.

Embodiment 6. The deployment system of any of Embodiments 1-5, wherein the ring component is translatingly arranged on the outer surface of the slider component.

Embodiment 7. The deployment system of any of Embodiments 1-6, wherein the slider track extends such that clockwise rotation of the ring component draws the cam toward the second end.

Embodiment 8. The deployment system of any of Embodiments 1-7, wherein the slider track extends in at least one circumferential direction and at least one longitudinal direction relative to the slider body.

Embodiment 9. The deployment system of any of Embodiments 1-8, wherein the cap comprises one or more indentations configured to provide grip features.

Embodiment 10. The deployment system of any of Embodiments 1-9, wherein the one or more indentations provide indicia regarding a degree of rotation of the crimping cam relative to the slider component.

Embodiment 11. The deployment system of any of Embodiments 1-10, wherein a further translational movement is required to draw the cam to the second end.

Embodiment 12. The deployment system of any of Embodiments 1-11, wherein the ring component defines two ring portions.

Embodiment 13. The deployment system of any of Embodiments 1-12, wherein the two ring portions have different circumferences.

Embodiment 14. The deployment system of any of Embodiments 1-13, wherein a ring portion extending less outwardly relative to the slider component of the two ring portions is arranged closer to the cap than a ring portion extending greater outwardly relative to the slider component of the two ring portions.

Embodiment 15. The deployment system of any of Embodiments 1-14, wherein the crimping cam defines a stop-forming detent configured to engage the cam at the second end to lock the crimping cam relative to the slider component.

Embodiment 16. A deployment system for a fixation device, the deployment system including a slider component defining a slider track on an outer surface thereof, a crimping cam slidably arranged within and concentric with the slider component and defining a stop-forming detent, and a locking component, wherein the locking component comprises a ring component rotatably arranged on the outer surface of the slider component, the ring component defining a cam on an inner diameter thereof configured to engage in a locked configuration with the stop-forming detent to lock rotation between the slider component and the crimping cam.

Embodiment 17. The deployment system of Embodiment 16, wherein the slider track extends in at least one circumferential direction and at least one longitudinal direction between a first end corresponding to an unlocked configuration and a second end corresponding to the locked configuration.

Embodiment 18. The deployment system of any of Embodiments 16-17, wherein the ring component is spaced longitudinally from a cap operably connected to the crimping cam by a distance corresponding to a predetermined distance through which the cam must be translated through the slider track to engage the stop-forming detent.

Embodiment 19. A method of deploying a fixation device, the method including providing a deployment system comprising a slider component defining a slider track on an outer surface thereof, a crimping cam slidably arranged within and concentric with the slider component, a cap operably connected to the crimping cam; and a locking component, the locking component comprising a ring component rotatably arranged on the outer surface of the slider component, the ring component defining a cam on an inner diameter thereof, rotating the ring component from a locked configuration to an unlocked configuration, and rotating the cap to rotate the crimping cam relative to the slider component to deploy the fixation device.

Embodiment 20. The method of deploying a fixation device of Embodiment 19, wherein the step of rotating the ring component from the locked configuration to the unlocked configuration further comprises the steps of: rotating the ring component circumferentially in a clockwise direction, and translating the ring component longitudinally by a predetermined distance to engage the cam with a stop-forming detent defined by the crimping cam.

Embodiment 21. The method of deploying a fixation device, wherein the deployment system is any one of Embodiments 1-19.

Embodiment 22. A fixation device, adapted to be incorporated into a delivery catheter handle, for restricting or arresting translation of a delivery catheter relative to a delivery catheter handle, wherein the fixation device includes a locking arm configured to extend between a locked configuration and an unlocked configuration, the locking arm further configured to rotate about a hinge comprising a pin extending through a portion of the locking arm and attaching to a body of the delivery catheter handle, wherein a body of the delivery catheter handle defines a recess configured to receive the locking arm, wherein when the locking arm is in the locking configuration, a protrusion defined by the locking arm presses against an outer diameter of a delivery catheter shaft to arrest or resist translation of the delivery catheter shaft relative to the delivery catheter handle.

Embodiment 23. A fixation device, adapted to be incorporated into a delivery catheter handle, for restricting or arresting translation of a delivery catheter relative to a delivery catheter handle, wherein the fixation device comprises an integrated screw provided on the delivery catheter handle and configured to translate circumferentially relative to the delivery catheter handle, wherein the integrated screw comprising a cap comprising a textured exterior surface and a threaded element connected to the cap, the threaded element configured to cooperate with an aperture defined by a body of the delivery catheter handle, the aperture defining threadings corresponding to the threaded element, the fixation device further comprising a brake element configured to apply compression to an outer diameter of a delivery catheter shaft as the integrated screw is moved in an insertion direction.

Embodiment 24. A deployment system, adapted to be incorporated into a delivery catheter handle, for restricting or arresting rotation of a crimping cam relative to a slider, wherein the deployment system comprises a cap attached to the crimping cam, the deployment system further comprising a ring extending generally concentrically and along an exterior surface of the slider, wherein the ring defines a cam extending inwardly from an internal surface of the ring and engaging a slot defined through at least a partial thickness of a body of the slider, wherein the slot defines a path extending at least longitudinally and/or circumferentially, the deployment system further comprising stop-forming terminal defined by the slot of the slider, the deployment system configured to facilitate rotation of the ring between a locked configuration in which the cam engages the stop-forming terminal and an unlocked configuration in which the cam does not engage the stop-forming terminal.

Embodiment 25. A deployment system, adapted to be incorporated into a delivery catheter handle, for restricting or arresting rotation of a crimping cam relative to a slider, wherein the deployment system comprises a cap comprising one or more fastening components facilitating releasable attachment of the cap to a bearing surface, the cap attached to the crimping cam, the bearing surface attached to an arm positioner, wherein the cap is configured to attach over and/or around the bearing surface in a substantially concentric manner, wherein the one or more fastening components extends through at least part of a thickness of the cap and the bearing surface to lock rotation of the cap and the crimping cam relative to the bearing surface.

Embodiment 26. A deployment system, adapted to be incorporated into a delivery catheter handle, for restricting or arresting rotation of a crimping cam relative to a slider, wherein the deployment system comprises a cap configured to be aligned with pins of the slider such that by compression of an exterior surface of the cap, pins of the cap push the pins of the slider inwardly within channels defined by the crimping cam, wherein the slider and the crimping cam are configured to rotate relative to each other upon a predetermined degree of inward movement of the pins of the slider.

Embodiment 27. A deployment system, adapted to be incorporated into a delivery catheter handle, for restricting or arresting rotation of a crimping cam relative to a slider, wherein the deployment system comprises a latch defined by a body of the slider and configured to toggle between a locked configuration and an unlocked configuration, the latch defining a profile corresponding to a profile of the slider, the latch defining a post configured to extend into a recess defined in a surface of the crimping cam.

Embodiment 28. A deployment system, adapted to be incorporated into a delivery catheter handle, for restricting or arresting rotation of a crimping cam relative to a slider, wherein the deployment system comprises a ring arranged slidably, translatingly, and/or concentrically on an exterior surface of an assembly through and into which an actuator rod extends, the assembly comprising a slider gear configured to translate a delivery catheter shaft and a deployment gear configured to rotate a crimping cam, the ring comprising a cam defined on an inner surface of the ring and corresponding to a cam slot defined through at least part of a thickness of the assembly, the cam slot defining a predetermined path between the slider gear and the deployment gear.

Embodiment 29. A deployment system, adapted to be incorporated into a delivery catheter handle, for restricting or arresting rotation of a crimping cam relative to a slider, wherein the deployment system comprises a bevel gear mechanism attached to the crimping cam, a knob connected to the bevel gear mechanism, and a post located generally opposite the bevel gear mechanism on a housing, the bevel gear mechanism configured to reduce a number of input turns from the knob to rotate the crimping cam and deploy a fixation device.

Embodiment 30. A deployment system, adapted to be incorporated into a delivery catheter handle, for restricting or arresting rotation of a crimping cam relative to a slider, wherein the deployment system comprises a button configured to toggle between a locked configuration and an unlocked configuration, wherein in the locked configuration the button is engaged within a recess defined by a body of the slider and extending into a recess defined within a thickness of the crimping cam, and wherein in the unlocked configuration the button does not couple the slider and the crimping cam, facilitating rotation therebetween.

Embodiment 31. A deployment system, adapted to be incorporated into a delivery catheter handle, for restricting or arresting rotation of a crimping cam relative to a slider, wherein the deployment system comprises a shield component pivoting from the slider between a locked and an unlocked configuration about a hinge defined in a thickness of the slider, the shield component defining a profile corresponding to a shape of the slider, wherein in the locked configuration the shield component extends generally continuously with the slider, and in the unlocked configuration the shield component extends generally up to a right angle with a surface of the slider, wherein in the locked configuration the shield component extends along substantially an entirety of a cap.

Embodiment 32. A deployment system, adapted to be incorporated into a delivery catheter handle, for restricting or arresting rotation of a crimping cam relative to a slider, wherein the deployment system comprises an outer ring extending concentrically about the slider and over a wedge component, the wedge component configured to extend through a body of the slider and into a recess defined by a surface of the crimping cam, the outer ring defining a cam slot corresponding to a cam defined by the wedge component and configured to extend circumferentially about the outer ring in a path configured to depress the wedge component into the recess defined by the surface of the crimping cam.

Embodiment 33. A deployment system, adapted to be incorporated into a delivery catheter handle, for restricting or arresting rotation of a crimping cam relative to a slider, wherein the deployment system comprises a handle extending beyond a surface of the slider and an arm connected to the handle and extending within a recess defined through at least a portion of a thickness of the slider such that the arm is generally coextensive with the surface of the slider, the handle further comprising a pin configured to extend through the slider and into a thickness of the crimping cam to arrest rotation of the crimping cam relative to the slider.

Embodiment 34. A deployment system, adapted to be incorporated into a delivery catheter handle, for restricting or arresting rotation of a crimping cam relative to a slider, wherein the deployment system comprises handle arranged to extend about an outer surface of the slider in a locked configuration, the handle pivotable relative to the slider to pivot between the locked configuration and an unlocked configuration, the handle connected to a deployment pin extending through channel defined by the slider and the crimping cam to lock rotation of the slider relative to the crimping cam, the handle further comprising a hinge connecting the handle to the deployment pin, the hinge configured to permit removal of the deployment pin when the handle is rotated to the unlocked configuration.

Embodiment 35. A method of deploying a fixation device, wherein the fixation device is any one of Embodiments 22-23.

Embodiment 36. The method of deploying a fixation device, wherein the deployment system is any one of Embodiments 1-19 and 24-34.

It will be understood that, unless a term is defined in this patent to possess a described meaning, there is no intent to limit the meaning of such term, either expressly or indirectly, beyond its plain or ordinary meaning.

It is to be understood that not necessarily all objects or advantages may be achieved under any embodiment of the disclosure. Those skilled in the art will recognize that the method, system, and device for deploying an implant embodiments may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to make or use a method, system, or device for deploying an implant under principles of the present disclosure. It will be understood by the skilled artisan that the features described may be adapted to other types of devices and processes. Hence this disclosure and the embodiments and variations thereof are not limited to mitral valve fixation devices and deployment systems, methods, and devices therefor, but can be utilized in any suitable process or device.

Although this disclosure describes certain exemplary embodiments and examples of a method, system, and device for deployment of an implant, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A deployment system for a fixation device, the deployment system comprising:
   a slider component defining a slider track on an outer surface thereof;
   a crimping cam slidably arranged within and concentric with the slider component, wherein the crimping cam defines a stop-forming detent configured to engage a cam at a second end of the stop-forming detent to lock the crimping cam relative to the slider component; and
   a locking component.

2. The deployment system of claim 1, wherein the locking component comprises a ring component rotatably arranged on the outer surface of the slider component, the ring component defining the cam on an inner diameter thereof.

3. The deployment system of claim 2, wherein the cam is configured to cooperate with the slider track, the slider track extending between a first end corresponding to an unlocked configuration and a second end corresponding to a locked configuration.

4. The deployment system of claim 2, wherein the ring component is translatingly arranged on the outer surface of the slider component.

5. The deployment system of claim 2, wherein in a locked configuration of the cam couples the slider component and the crimping cam, preventing rotation therebetween.

6. The deployment system of claim 5, wherein the slider track extends in at least one circumferential direction and at least one longitudinal direction relative to a slider body.

7. The deployment system of claim 5, wherein the slider track extends such that clockwise rotation of the ring component draws the cam toward the second end.

8. The deployment system of claim 7, wherein a further translational movement is required to draw the cam to the second end.

9. The deployment system of claim 1, further comprising a cap operably connected with the crimping cam.

10. The deployment system of claim 9, wherein the cap comprises one or more indentations configured to provide grip features.

11. The deployment system of claim 10, wherein the one or more indentations provide indicia regarding a degree of rotation of the crimping cam relative to the slider component.

12. The deployment system of claim 1, wherein the locking component comprises a ring component rotatably arranged on the outer surface of the slider component, wherein the ring component defines-a first ring portion and a second ring portion.

13. The deployment system of claim 12, wherein the first ring portion and the second ring portion have different circumferences.

14. The deployment system of claim 13, wherein the first ring portion has a smaller diameter than the second ring portion, the first ring portion being arranged closer to the cap than the second ring portion.

15. A deployment system for a fixation device, the deployment system comprising:
   a slider component defining a slider track on an outer surface thereof;

a crimping cam slidably arranged within and concentric with the slider component and defining a stop-forming detent; and a locking component;

wherein the locking component comprises a ring component rotatably arranged on the outer surface of the slider component, the ring component defining a cam on an inner diameter thereof configured to engage in a locked configuration with the stop-forming detent to lock rotation between the slider component and the crimping cam.

16. The deployment system of claim 15, wherein the slider track extends in at least one circumferential direction and at least one longitudinal direction between a first end corresponding to an unlocked configuration and a second end corresponding to the locked configuration.

17. The deployment system of claim 16, wherein the ring component is spaced longitudinally from a cap operably connected to the crimping cam by a distance corresponding to a predetermined distance through which the cam must be translated through the slider track to engage the stop-forming detent.

* * * * *